US00RE38444E

(19) United States
(12) Reissued Patent
Wada et al.

(10) Patent Number: US RE38,444 E
(45) Date of Reissued Patent: Feb. 24, 2004

(54) ABSORBING AGENT, PROCESS OF MANUFACTURING SAME, AND ABSORBENT PRODUCT CONTAINING SAME

(75) Inventors: Katsuyuki Wada, Himeji (JP); Kinya Nagasuna, Nara (JP); Shin-ichi Fujino, Himeji (JP); Yoshihiko Masuda, Takarazuka (JP)

(73) Assignee: Nippon Shokubai Co., Ltd., Osaka (JP)

(21) Appl. No.: 09/586,745

(22) PCT Filed: Dec. 28, 1995

(86) PCT No.: PCT/JP95/01150

§ 371 (c)(1),
(2), (4) Date: Jun. 9, 1995

(87) PCT Pub. No.: WO95/34377

PCT Pub. Date: Dec. 21, 1995

Related U.S. Patent Documents

Reissue of:
(64) Patent No.: 5,760,080
Issued: Jun. 2, 1998
Appl. No.: 08/571,960
Filed: Dec. 28, 1995

(30) Foreign Application Priority Data

Jun. 13, 1994 (JP) ..... 6-130385
Jun. 14, 1994 (JP) ..... 6-132126

(51) Int. Cl.[7] ..... C08F 8/32; C08F 8/14

(52) U.S. Cl. ..... 524/559; 525/328.3; 525/328.5; 525/329.4; 525/329.5; 525/380; 525/382; 525/384

(58) Field of Search ..... 524/559; 525/328.3, 525/328.5, 329.4, 329.5, 380, 382, 384

(56) References Cited

U.S. PATENT DOCUMENTS

| | | | | |
|---|---|---|---|---|
| 4,654,039 A | | 3/1987 | Brandt et al. | 604/368 |
| 4,666,975 A | | 5/1987 | Yamasaki et al. | 542/733 |
| RE32,649 E | | 4/1988 | Brandt et al. | 604/368 |
| 5,026,800 A | | 6/1991 | Kimura et al. | 526/200 |
| 5,061,259 A | | 10/1991 | Goldman et al. | 604/368 |
| 5,147,343 A | | 9/1992 | Kellenberger | 604/368 |
| 5,149,334 A | | 9/1992 | Lahrman et al. | 604/367 |
| 5,149,335 A | | 9/1992 | Kellenberger et al. | 604/372 |
| 5,236,427 A | | 8/1993 | Hamajima et al. | 604/378 |
| 5,300,565 A | | 4/1994 | Berg et al. | 525/54.2 |
| 5,314,420 A | | 5/1994 | Smith et al. | 604/358 |
| 5,385,983 A | * | 1/1995 | Graham | 525/330.1 |
| 5,409,771 A | | 4/1995 | Dahmen et al. | 428/327 |
| 5,442,405 A | | 8/1995 | Taniguchi et al. | 525/384 |
| 5,597,873 A | | 1/1997 | Chambers et al. | 525/330.1 |
| 5,610,208 A | | 3/1997 | Dairoku et al. | 525/384 |

FOREIGN PATENT DOCUMENTS

| | | |
|---|---|---|
| DE | 40 20 780 C1 | 8/1991 |
| EP | 0 530 438 A1 | 3/1993 |
| EP | 0 532 002 A1 | 3/1993 |
| EP | 0 555 692 A1 | 8/1993 |
| EP | 0 304 319 B1 | 2/1994 |
| JP | 49-43395 B | 11/1974 |
| JP | 51-125468 A | 1/1976 |
| JP | 52-14689 A | 3/1977 |
| JP | 53-15959 B | 5/1978 |
| JP | 55-84304 A | 6/1980 |
| JP | 55-108407 A | 8/1980 |
| JP | 55-133413 A | 10/1980 |
| JP | 58-154709 A | 9/1983 |
| JP | 58-154710 A | 9/1983 |
| JP | 63-21902 A | 1/1988 |
| JP | 63-99861 A | 5/1988 |
| JP | 63-275608 A | 11/1988 |
| JP | 1-292004 A | 11/1989 |
| JP | 2-34167 A | 2/1990 |
| JP | 2-242809 A | 9/1990 |
| JP | 3-56513 A | 3/1992 |
| WO | WO 94/09043 | 4/1994 |

* cited by examiner

*Primary Examiner*—Bernard Lipman
(74) *Attorney, Agent, or Firm*—Kubovcik & Kubovcik

(57) ABSTRACT

An absorbing agent has a diffusing absorbency under pressure of not less than 25 g/g when 60 minutes elapsed after absorption is started, and a water-soluble content is above 0 percent by weight and not more than 7 percent by weight. The absorbing agent is prepared by surface-crosslinking a precursor of the absorbing agent obtained by performing an aqueous solution polymerization of a hydrophilic unsaturated monomer having not less than 50 mole percent neutralized acrylic acid as a main component using a specific crosslinking agent having a main component composed of an ester compound of a specific polyhydroxy alcohol and an unsaturated carboxylic acid, and a high-boiling component having at least two alcohol structures in a molecule as a specific ratio. As a result, an absorbing agent having excellent properties such as the diffusing absorbency under pressure is high, the water soluble content is small, and the amount of wet back of the aqueous liquid after a long period of time is small, water absorbency under pressure can be stably maintained for a long period of time can be achieved.

29 Claims, 7 Drawing Sheets

ABSORBING AGENT, PROCESS OF MANUFACTURING SAME, AND ABSORBENT PRODUCT CONTAINING SAME

Matter enclosed in heavy brackets [ ] appears in the original patent but forms no part of this reissue specification; matter printed in italics indicates the additions made by reissue.

FIELD OF THE INVENTION

The present invention relates to an absorbing agent suited for use in sanitary goods such as paper diaper (disposable diaper), sanitary napkin, incontinence pad, etc., and a method of manufacturing the same and also relates to an absorbent product containing such absorbing agent.

BACKGROUND OF THE INVENTION

Recently, an absorbent resin is widely used in sanitary goods such as paper diaper, sanitary napkin, incontinence pad, etc., for the purpose of absorbing liquid.

Examples of known absorbent resins include: a partially neutralized crosslinked polymer of polyacrylic acid (Japanese Laid-Open Patent Publication No. 84304/1980 (Tokukaisho 55-84304), Japanese Laid-Open Patent Publication No. 108407/1980 (Tokukaisho 55-108407) and Japanese Laid-Open Patent Publication No. 133413/1980 (Tokukaisho 55-133413)); a hydrolyzed graft polymer of starch-acrylonitrile (Japanese Examined Patent Publication No. 43995/1974 (Tokukosho 46-43995)); a neutralized graft polymer of starch-acrylic acid (Japanese Laid-Open Patent Publication No. 125468/1976 (Tokukaisho 51-125468)); a saponified copolymer of vinyl acetate-acrylic ester (Japanese Laid-Open Patent Publication No. 14689/1977 (Tokukaisho 52-14689)); a hydrolyzed copolymer of acrylonitrile or of acrylamide (Japanese Examined Patent Publication No. 15959/1978 (Tokukosho 53-15959)); a crosslinked polymer of cationic monomer (Japanese Laid-Open Patent Publication No. 154709/1983 (Tokukaisho 58-154709) and Japanese Laid-Open Patent Publication No. 154710/1983 (Tokukaisho 58-154710)).

Notable properties of the absorbent resin include absorbing capacity and absorbency under pressure when it is in contact with an aqueous liquid like a body fluid, gel strength, and absorbing power of absorbing liquid from a base material containing an aqueous liquid, etc. Conventionally, the absorbent resins having some of the above-mentioned properties which show desirable properties (absorption properties) in their applications of paper diaper, sanitary napkin, etc., as well as absorbent materials and the absorbent product using such absorbent resins have been proposed.

Examples of such absorbent resins, absorbent materials and absorbent products include: an absorbent resin disclosing a combination of a specific gel capacity, shear modulus and an extraction polymer content (U.S. Pat. No. 4,654,039); an absorbent resin having predetermined ranges of absorbing capacity and absorbency under pressure and gel stability, and a paper diaper and a sanitary napkin using such absorbent resin (Japanese Laid-Open Patent Publication No. 185550/1985 (Tokukaisho 60-185550)), (Japanese Laid-Open Patent Publication No. 185551/1985 (Tokukaisho 60-185551)) and (Japanese Laid-Open Patent Publication No. 185804/1985 (Tokukaisho 60-185804)); a paper diaper using an absorbent resin having predetermined ranges of absorbing capacity, absorbency under pressure and a gel stability (Japanese Laid-Open Patent Publication No. 185805/1985 (Tokukaisho 60-185805)); an absorbent product having predetermined absorbing capacity, absorbing power and water soluble content (Japanese Laid-Open Patent Publication No. 21902/1988 (Tokukaisho 63-21902)); an absorbent sanitary product including an absorbent resin having predetermined ranges of absorbing capacity, absorbing capacity under pressure, and a gel breaking strength (Japanese Laid-Open Patent Publication No. 99861/1988 (Tokukaisho 63-99861)); a paper diaper including an absorbent resin having predetermined ranges of absorbing capacity and absorbency under pressure (Japanese Laid-Open Patent Publication No. 34167/1990 (Tokukaihei 2-34167)); an absorbing agent containing an absorbent resin having predetermined ranges of absorbing capacity under pressure and particle diameter (European Patent No. 339,461); an absorbing agent including at least a predetermined amount of an absorbent resin having predetermined ranges of absorbency under pressure and absorbing capacity under pressure in a short period of time (European Patent No. 443,627); an absorbing synthetic material having at least predetermined amount of absorbent resin having predetermined ranges of deformation and absorbing index when applying a load (European Patent No. 532,002).

Recently, still thinner sanitary goods such as a paper diaper and a sanitary napkin of higher quality have been demanded, and an amount of use of the absorbent resin or weight percent of the absorbent resin in the absorbent material mainly composed of absorbent resin and hydrophilic fiber (hereinafter simply referred to as a resin concentration) has been increasing. Namely, by reducing the amount of hydrophilic fiber having a small bulk specific gravity and increasing the amount of the absorbent resin having a large bulk specific gravity, the ratio of the absorbent resin in the absorbent material is raised, and a thinner sanitary material can be achieved without reducing the absorbing capacity.

However, earnest researches have been made by the inventors of the present invention in order to increase the absorbing amount of the sanitary material, for example, by increasing the resin concentration in the absorbent material. As a result, the inventors have found that the absorbent material having a higher resin concentration than conventional absorbent material cannot be used without having problems such as leakage of aqueous liquid from the sanitary goods, etc., only by controlling the described absorbing capacity, absorbency under pressure, gel strength, absorbing capacity, etc. For example, as to the absorbent resin which has been viewed with interest in which only absorbing capacity under pressure is large, by raising the resin concentration, the liquid dispersability of the absorbent material is significantly reduced.

Further researches have been made by the inventors on absorbing properties of the absorbent material having higher resin concentration than conventional absorbent material. As a result, they have found that in the case of using a mixture of a known absorbent resin, a hydrophilic fiber is used as an absorbent material, although when a resin concentration is low, the absorbent material shows a predetermined level of absorbing properties, when a resin concentration is above 40 percent by weight, such unpreferable conditions that the liquid dispersibility is rapidly lowered, the absorbing capacity of weight per unit of the absorbent material is lowered, the water absorbing capacity cannot be ensured for a long period of time; an amount of wet back of the aqueous liquid increases, etc., would occur. Namely, when a mixture of the known absorbent resin and the hydrophilic fiber is used as an absorbent material, the above-mentioned problems would arise.

Accordingly, an object of the present invention is to eliminate the above-mentioned problems and to provide an absorbing agent having excellent properties (absorbing properties) such as very high liquid diffusivity and a stability over time of the absorbing capacity irrespectively of the resin concentration or the structure of the absorbent material, for example, when it is used as sanitary goods, etc., as well as a process of manufacturing such absorbing agent and the absorbent product including the absorbing agent.

Another object of the present invention is to provide an absorbing agent having excellent properties (absorbing properties, etc.,) of maintaining very high liquid diffusivity and absorbing capacity even with high resin concentration.

[Disclosures of the Invention]

In order to achieve the above object, earnest researches on the absorbing agent and the manufacturing method thereof have been made by inventors of the present invention. As a result, an absorbing agent obtained by synthesizing the precursor of the absorbing agent by performing an aqueous solution polymerization of the hydrophilic unsaturated monomer having more than 50 mole percent neutralized acrylic acid as a main component in the presence of the crosslinking agent and dispersant, and applying a heat treatment in a presence of a surface crosslinking agent after adjusting the precursor of the absorbing agent so as to have a predetermined range of water content and a predetermined range of the particle diameter, exhibit excellent properties such as very high liquid diffusivity and stable absorbing capacity over time. Namely, the absorbing agent obtained by synthesizing the precursor of the absorbing agent and applying the heat treatment in a presence of a specific surface crosslinking agent, the absorbent material and the absorbent product including such absorbing agent exhibit excellent performances such as very high liquid diffusivity, absorbing capacity, etc., even when the amount of use of the absorbent resin and the resin concentration are high.

Namely, in order to solve the above-mentioned problem, an absorbing agent of the present invention is characterized in that the diffusing absorbency under pressure measured when 60 minutes has elapsed after an absorption is started is 25 g/g.

In order to solve the above-mentioned problem, the absorbent material of the present invention may be characterized by including not less than 40 percent by weight of the absorbing agent.

In order to solve the above-mentioned problem, the absorbent material of the present invention may be characterized in that its diffusing absorbency under pressure measured when 60 minutes has elapsed after the absorption is started is not less than 25 g/g, and the water soluble content is above 0, and the absorbing agent is not more than 7 percent by weight.

The following will explain the present invention in details.

The diffusing absorbency under pressure in the present invention suggests a new property value for evaluating the absorbency under pressure of the absorbing agent and the absorbent material in view of the diffusivity of the aqueous liquid wherein the weighing capacity of the absorbent resin is high and resin particles are tightly linked one another by an external force.

The diffusing absorbency under pressure is computed based on values measured when a predetermined time elapsed after the absorption is started under predetermined conditions, for example, after 20 minutes, 30 minutes, and 60 minutes, etc. The method of measuring the diffusing absorbency under pressure will be explained in below-mentioned embodiments.

The diffusing absorbency under pressure enables evaluations of new properties of the absorbing agent, the absorbent material, i.e., the absorbent resin. Namely, the diffusing absorbency under pressure evaluates the uniformity and the diffusivity of the absorbent resin in the aqueous liquid in a resin layer direction (hereinafter simply referred to as a lateral direction), or an actual absorbing capacity of the absorbent resin as a whole. The liquid diffusivity in a lateral direction (liquid diffusivity and liquid transmissivity) is an important factor of absorbing a large amount of aqueous liquid. Based on the results of evaluation, for example, the absorbing ability of the absorbent material mainly composed of the absorbing agent (absorbent resin) and hydrophilic fiber can be easily estimated especially in the absorbent resin in the absorbent material having high percent by weight (hereinafter referred to as a resin concentration) of the absorbent resin. The configuration of the absorbent material will be explained later.

Many prior art applications disclose evaluations of the absorbing capacity under pressure. However, in conventional methods, the absorbing capacity is evaluated only in the direction orthogonal to the resin layer direction (hereinafter simply referred to as a longitudinal direction). Therefore, in this method, the uniformity and the diffusivity of the aqueous liquid are hardly known. Therefore, from the conventional evaluation results, the absorbing capacity of the absorbent material in a paper diaper, etc., adopting the absorbent material having a high resin concentration cannot be estimated accurately.

The water soluble content in the present invention suggests property values for evaluating the rediffusivity of the aqueous liquid after a long time elapsed when the absorbent resin has excellent diffusing absorbency under pressure and evaluating the ability of maintaining absorbed aqueous liquid for a long period of time. The described water soluble content is measured under predetermined conditions. The method of measuring the water soluble content will be described in detail in the below-mentioned embodiments.

Even if the absorbent resin has excellent diffusing absorbency under pressure, if the water soluble content thereof is outside the predetermined range of the present invention, the amount of wet back of the aqueous liquid after a long period of time elapsed tends to increase. On the other hand, the absorbing agent, i.e., the absorbent resin of the present invention satisfies both the diffusing absorbency under pressure and the water soluble content. The absorbing agent having excellent properties such as very high liquid diffusivity and stable absorbing capacity for a long period of time without being much affected by the configuration of the resin concentration or the absorbent material, etc., the process of manufacturing thereof and the absorbent product including such absorbing agent will be explained.

The absorbing agent of the present invention has the diffusing absorbency under pressure of not less than 25 g/g and the water soluble content of not more than 7 percent by weight. In the absorbing agent, i.e., the absorbent resin having the diffusing absorbency under pressure of less than 25 g/g, i.e., the absorbent resin, the liquid diffusivity in the lateral direction in the absorbent material (high concentration) with an increased resin concentration is deteriorated, and the absorbing capacity of the absorbent material is lowered. In the present invention, it is preferable that the diffusing absorbency under pressure is not less than 28 g/g, more preferably not less than 30 g/g, and most preferably not less than 32 g/g. Even if the absorbent resin has the diffusing absorbency under pressure of not less than 25 g/g, if the water soluble content is above 7 percent by weight, the amount of wet back of the aqueous liquid after a long time elapsed would increase. It is preferable that the water soluble content is not more than 5 percent by weight, and more preferably not more than 3 percent by weight. In the present invention, the diffusing absorbency under pressure is determined by values measured when 60 minutes has elapsed after the absorption is started under predetermined conditions. In addition, the absorbing agent having the diffusing absorbency under pressure of not less than 15 g/g computed from the value measured when 20 minutes has elapsed after the absorption is started is preferable, and those having the diffusing absorbency under pressure of not less than 20 g/g is more preferable.

The absorbent product of the present invention is characterized by including the absorbing agent having the described excellent properties as the absorbent material. However, other than the absorbing agent, such absorbent material may include hydrophilic fiber when an occasion demands. Examples of the structures of the absorbent material in the case where the absorbent material composed of, for example, the absorbing agent and a hydrophilic fiber include: the structure wherein an absorbing agent and a hydrophilic fiber are uniformly mixed; a structure wherein the absorbing agent is sandwiched between layered hydrophilic fiber; a structure wherein the absorbing agent and the hydrophilic fiber are homogeneously mixed so as to form a layer and a hydrophilic fiber is formed thereon; the structure wherein the absorbing agent is sandwiched between the layered hydrophilic fiber and the layer formed of mixing uniformly the absorbing agent and the hydrophilic fiber. Furthermore, the absorbent material is obtained by forming the absorbing agent in a sheet by mixing a predetermined amount of water with respect to the absorbing agent. In addition, the structure of the absorbent material is not limited to the exemplified structure.

Examples of the hydrophilic fiber include: a cellulose fiber such as a mechanical pulp, a chemical pulp, a semi-chemical pulp, a dissolved pulp, etc.; an artificial cellulose fiber such as rayon, acetate, and the like. Among the above-listed fiber, cellulose fiber is preferable. The hydrophilic fiber may include a synthetic fiber such as polyamide, polyester, polyolefin, etc. The hydrophilic fiber of the present invention is not limited to the above-listed fibers.

To obtain excellent properties, the absorbing agent of the present invention is characterized in that it is preferable that the ratio of the hydrophilic fiber in the absorbent material is above 0, and not more than 60 percent by weight, more preferably not less than 20 percent by weight and not more than 40 percent by weight. The higher is the resin concentration of the absorbent material, the more obvious are the properties of the absorbing agent and the absorbent material. The performances of the absorbent resin of the present invention can be fully exhibited irrespectively of the ratio of the hydrophilic fiber in the absorbent material. In addition, the performances of the absorbing agent are hardly affected by the described configuration of the absorbent material.

When the ratio of the hydrophilic fiber in the absorbent material is relatively small, the absorbent material, namely the hydrophilic fibers may be linked by using an adhesive binder. By linking the hydrophilic fiber, the strength and the shape retention before and while using the absorbent material can be high.

Examples of such adhesive binder include: thermal fusing fiber such as polyethylene, polypropylene, ethylene-propylene copolymer, 1-butene-ethylene copolymer, and the like, emulsion having an adhesive property, etc. Only one kind of the above-listed adhesive binder may be adopted, or two or more kinds thereof may be suitably mixed and adopted. The ratio by weight of the hydrophilic fiber to the adhesive binder is preferably in a range of 50/50–99/1, more preferably in a range of 70/30–95/5, still more preferably in a range of 80/20–95/5.

The absorbing agent in accordance with the present invention is produced in the following manner. First, a precursor of the absorbing agent is prepared by performing an aqueous solution polymerization of hydrophilic unsaturated monomer having at least 50 mole percent neutralized acrylic acid as a main component in a presence of a crosslinking agent and a dispersant using a certain amount of the crosslinking agent having a specific composition. Then, the precursor of the absorbing agent is adjusted so as to have a specific range of water content and a particle diameter of a specific range. Thereafter, a heat treatment is applied to the precursor of the absorbing agent in the presence of the surface crosslinking agent.

The hydrophilic unsaturated monomer used as a raw material of the present invention includes acrylic acid and a neutralized material thereof as a main component. To improve the water absorbing properties of the water-absorbing agent, it is preferable that at least 50 mole percent is neutralized by alkali metal salt, ammonium salt, amine salt, etc. Furthermore, to still improve the absorbing properties of the absorbing agent, it is still preferable that around 65 mole percent to 80 mole percent of the acrylic acid is neutralized.

The hydrophilic unsaturated monomer may include an unsaturated monomer other than acrylic acid. Such unsaturated monomer other than acrylic acid is not especially limited. However, such examples include: an anionic unsaturated monomer such as methacrylic acid, maleic acid, vinylsulfonic acid, styrenesulfonic acid, 2-(meth) acrylamide-2-methylpropanesulfonic acid, 2-(meth) acryloylethanesulfonic acid, 2-(meth) acryloylpropanesulfonic acid, etc., and salts thereof; a nonionic unsaturated monomer including hydrophilic groups such as acrylamide, methacrylamide, N-ethyl(meth) acrylamide, N-n-propyl (meth)acrylamide, N-isopropyl (meth)acrylamide, N,N-dimethyl(meth)acrylamide, 2-hydroxyethyl(meth)acrylate, 2-hydroxypropyl (meth) acrylate, methoxypolyethylene glycol (meth)acrylate, polyethylene glycol mono(meth) acrylate, vinylpyridine, N-vinylpyrrolidone, N-acryloylpiperidine, N-acryloylpyrrolidine and the like; a cationic unsaturated monomer such as N,N-dimethyl aminoethyl(meth)acrylate, N,N-diethyl aminoethyl(meth) acrylate, N,N-dimethyl aminopropyl(meth)acrylate, N,N-dimethyl aminopropyl (meth)acrylamide and quaternary salts thereof and the like.

The above-mentioned additional hydrophilic unsaturated monomer is preferably used in an amount not more than 50 percent by weight with respect to the total amount of the acrylic acid and the neutralized product thereof used as a main component.

The crosslinking agent of the present invention is obtained by the esterification reaction of polyhydroxy alcohol having not more than six carbon atoms and at least three hydroxy groups (hereinafter referred to as a polyhydroxy alcohol) and an unsaturated carboxylic acid among unsaturated carboxylates such as acrylate having plural functional groups (hereinafter referred to as polyfunctional); or an transesterification of polyhydroxy alcohol having at least three hydroxy groups and a unsaturated carboxylic ester. However, it is difficult to industrially produce the unsaturated carboxylic ester wherein all the hydroxyl groups of polyhydroxy alcohol having at least three hydroxy groups and the unsaturated carboxylic acid are ester exchanged, i.e., a desired unsaturated carboxylic ester at high selectivity and high yield at low cost. Depending on reaction conditions, normally, when synthesizing the unsaturated carboxylic ester, in addition to the desired unsaturated carboxylic ester, a large amount of a high boiling-point compound having at least two polyhydroxy alcohol structures in a molecule is generated.

Inventors of the present invention made earnest researches to achieve the absorbent resin of improved performances prepared by performing an aqueous solution polymerization of hydrophilic unsaturated monomer using industrially available unsaturated carboxylic ester, i.e., unsaturated carboxylic ester including such high-boiling point compound as a crosslinking agent. As a result, they have found that when performing a polymerization reaction of unsaturated carboxylate containing the high-boiling point compound, it is difficult to improve the diffusing absorbency under pressure of the absorbing agent and to decrease the amount of water-soluble component. Thus, further researches have been made by the inventors to obtain the absorbent resin (i.e., the absorbing agent) which shows excellent properties including diffusing absorbency under pressure and liquid diffusivity, etc., and contains smaller amount of water soluble content. As a result, only when the crosslinking agent adjusted so as to have a predetermined range of the high-boiling point component is used in a specific amount in the presence of the dispersant, the absorbing agent having a small amount of the water-soluble content and improved absorbency under pressure, etc., can be achieved.

Namely, the crosslinking agent of the present invention is composed of an ester compound of a polyhydroxy alcohol having not more than six carbon atoms and at least three hydroxy groups and an unsaturated carboxylic acid, wherein a ratio in molecular weight of the compound to a standard compound in which all the hydroxy groups in polyhydroxy alcohol having at least three hydroxy groups are ester-linked to the unsaturated carboxylic acid is in the range of from 0.7/1 to less than 1.3/1, and a high-boiling point component having at least two alcohol structures, and a weight ratio of the main component of the crosslinking agent to the high boiling point component in a range of 75/25–99/1.

The alcohol having at least three hydroxy groups used in preparing the crosslinking agent is not specified. However, preferable examples of the alcohols include: glycerin, trimethylolethane, tetramethylolethane, trimethylolpropane, tetrahydroxyethane, pentaerythritol, etc. Among the above listed alcohols, trimethylolpropane is especially preferable. For the unsaturated carboxylic acid used in the preparation of the crosslinking agent, any of the previously listed hydrophilic unsaturated monomers having at least one carboxyl group may be used. However, acrylic acid is especially preferable.

As described, the main component of the crosslinking agent may be a compound in which a ratio in molecular weight of the compound to a standard compound wherein all the hydroxyl groups of the polyhydroxy alcohol having at least three hydroxy groups are ester-linked to the unsaturated carboxylic acid among multifunctional unsaturated carboxylates which include polyhydroxy alcohol having at least three hydroxy groups as a alcohol component and an unsaturated carboxylic acid as an acid component is in a range between 0.7 to less than 1.3.

For example, in the case where the trimethylolpropane is used as a polyhydroxy alcohol having at least three hydroxy groups and acrylic acid is used as an unsaturated carboxylic acid, examples of the main component of the crosslinking agent include: trimethylolpropane triacrylate; trimethylolpropane diacrylate; trimethylolpropane diacrylatemono (β-acryloyloxypropionate), and the like. In the case where glycerin is used as polyhydroxy alcohol having at least three hydroxy groups, and acrylic acid is used as unsaturated carboxylic acid as the main component of the crosslinking agent, examples of the main component of the crosslinking agent include: glycerintriacrylate, glycerinditriacrylate, etc. In the case where trimethylolethane is used as polyhydroxy alcohol having at least three hydroxy groups, and acrylic acid is used as unsaturated carboxylic acid as the main component of the crosslinking agent, examples of the main component of the crosslinking agent include: trimethylolethanetriacrylate, trimethylolethane diacrylate, and the like. In the case where the tetramethylolethane is used as polyhydroxy alcohol having at least three hydroxy groups and acrylic acid is used as unsaturated carboxylic acid, examples of the main component of the crosslinking agent include: tetramethylol ethane tetracrylate, tetramethylolethane triacrylate, etc. In the case where tetrahydroxyethane is used as polyhydroxy alcohol having at least three hydroxy groups and acrylic acid is used as an unsaturated carboxylic acid, examples of the main component of the present invention include tetrahydroxyethane tetracrylate, tetrahydroxy ethane triacrylate, and the like. In the case where pentaerythritol is used as polyhydroxy alcohol having at least three hydroxy groups and acrylic acid as unsaturated carboxylic acid, penthaerythritol tetracrylate, pentaerythritol triacrylate, etc., may be used.

The high-boiling point compound included in the crosslinking agent having a complicated structure is a by-product generated when synthesizing the main component of the crosslinking agent. For example, in the case where the trimethylolpropane is used as the polyhydroxy alcohol having at least three hydroxy groups and acrylic acid is used as an unsaturated carboxylic acid, examples of the high-boiling point component include: condensation products having at least two trimethylol propane structures in a molecule such as a compound generated from an additional reaction of trimethylolpropane triacrylate and trimethylolpropane diacrylate, a dimer of trimethylolpropane diacrylate, a compound generated by an additional reaction between trimethylolpropane diacrylate and trimethylolpropane monoacrylate, etc.

In the present invention, it is necessary to satisfy the condition that the weight ratio of the crosslinking agent main component and the high boiling point component in the crosslinking agent is in a range of 75/25–99/1, and preferably in a range of 80/20–90/10. When the weight ratio of the main component of the crosslinking agent to the high boiling point component in the crosslinking agent is less than 75/25, i.e., when the ratio of the main component of the crosslinking agent to the total amount of the crosslinking agent main component and the high boiling point component is less than 75 percent by weight (i.e., when the ratio of the high boiling point is above 25 percent by weight), even when the dispersant of the present invention is used, an absorbing agent which shows excellent diffusing absorbency under pressure and the liquid diffusivity and the absorbing agent having a smaller amount of water soluble content cannot be achieved. On the other hand, it is difficult to obtain a crosslinking agent in which the ratio in weight of the crosslinking agent main component and the high boiling component is above 99/1, i.e., the crosslinking agent in which the ratio of the main component with respect to the total amount of the main component of the crosslinking agent and the high boiling point component is above 99 percent by weight (i.e., the ratio of the high-boiling point component is less than 1 percent by weight) is not easily obtainable. Therefore, it is not industrially preferable. In addition, even when using the crosslinking agent having the main component ratio of the crosslinking agent of above 99 percent by weight, compared to the case of using the crosslinking agent in an amount of 75 percent by weight to 99 percent by weight, significant effects cannot be achieved.

The amount of use of the crosslinking agent is not less than 0.05 mole percent and not more than 0.5 mole percent with respect to the hydrophilic unsaturated monomer, and it is preferably not less than 0.07 mole percent and not more than 0.2 mole percent. When the amount of use of the crosslinking agent is less than 0.05 mole percent or above 0.5 mole percent, the diffusing absorbency under pressure of the absorbing agent is lowered, and the amount of the water-soluble content increases. Therefore, it is industrially unpreferable. In the polyfunctional unsaturated carboxylates having a polyhydroxy alcohol having at least three hydroxy groups and acrylic acid as an acid component, the amount of use of the crosslinking agent should be calculated based on the compound wherein all the hydroxy groups of the polyhydroxy alcohol having at least three hydroxy groups are ester-linked to the unsaturated carboxylates, i.e, based on the molecular weight of the main component of the crosslinking agent.

For the dispersant used in the aqueous solution polymerization of the present invention, a compound which is homogeneously dissolved in water and is compatible with the crosslinking agent is preferable, and in general, industrially obtainable compounds are preferable. Examples of such dispersant include: a nonionic surface active agent such as sorbitan aliphatic acid ester, polyoxyethylene sorbitan aliphatic ester, polyglycerin aliphatic ester, polyoxyethylene alkyl ether, polyoxyethylene alkyl phenol ether, polyoxyethylene acyl ether, cane sugar aliphatic acid ester, and the like; an anionic surface active agent such as higher alcohol sulfate ester, alkyl naphthalene sulfonic acid salt, alkylpolyoxyethylene sulphate salt, dialkyl sulfosuccinate, and the like; a cationic surface active agent such as alkyl quarternary ammonium salts, alkyl amine salts, and the like; an amphoteric surface active agent such as alkylbetaine, lecithin, etc., a polymer compound such as a lipophilic polymer having a carboxyl group, a partially saponificated polyvinyl alcohol, methyl cellulose, carboxymethyl cellulose, hydroxyethylcellulose, etc. Among the above-listed dispersants, a water soluble surface active agent, and water diffusible surface active agent are preferable, and a nonionic surface active agent having at least 10 HLB (hydrophilic-lipophilic balance) is the most preferable. The amount of use of the dispersant is preferably in the range of 1–100 percent by weight with respect to the crosslinking agent, more preferably in the range of 5–50 percent by weight. The amount of use of the dispersant is preferably in the range of 0.005–0.5 parts by weight with respect to 100 parts by weight of the precursor of the absorbing agent resulting from the hydrophilic unsaturated monomer.

The method of mixing (adding) the dispersant in the aqueous solution polymerization is not especially limited. For example, after directly mixing the crosslinking agent and the dispersant, the mixed solution may be mixed with the hydrophilic unsaturated monomer or aqueous solution thereof. Alternatively, after mixing the solution or dispersion liquid of the crosslinking agent and the dispersant, the hydrophilic unsaturated monomer or the solution thereof may be mixed. After mixing the crosslinking agent, the dispersant, the hydrophilic unsaturated monomer, or a part of the solution, the resulting mixed solution may be mixed with the rest of the hydrophilic unsaturated monomer and/or the solution. Or after mixing the crosslinking agent, the solution or dispersion liquid of the dispersant and a part of hydrophilic unsaturated monomer or the solution thereof, the resulting solution may be mixed with the rest of the hydrophilic unsaturated monomer or the solution thereof. Among the above-listed mixing processes, the process wherein after mixing the crosslinking agent, the dispersant and a part of the hydrophilic unsaturated monomer or the solution thereof, the resulting mixed solution is mixed with the rest of hydrophilic unsaturated monomer or the solution thereof is preferable. Further, the process wherein after mixing the crosslinking agent, the dispersant, and a part of the acrylic acid as hydrophilic unsaturated monomer, or the solution thereof, the resulting mixed solution may be mixed with the rest of the hydrophilic unsaturated monomer or the solution thereof (neutralized polymer of acrylic acid) is more preferable.

When performing a polymerization of a hydrophilic unsaturated monomer in the presence of the crosslinking agent and the dispersant, the concentration of the hydrophilic unsaturated monomer in solution is preferably in the range from 25 percent by weight to a concentration (percent by weight) at the saturation point, more preferably in the range between 30 percent by weight and 45 percent by weight.

When starting the polymerization by the polymerization reaction, for example, a radical polymerization initiator such as potassium persulfate, ammonium persulfate, sodium persulfate, t-butylhydroperoxide, hydrogen peroxide, 2,2'-azobis(2-amidinopropane)dihydrochloride, etc., or an active energy ray, such as an ultraviolet ray, or an electron ray, etc., may be used. In the case of employing an oxidative radical polymerization initiator, a redox polymerization may be carried out by simultaneously using a reducing agent such as sodium sulfite, sodium hydrogen sulfite, ferrous sulfate, L-ascorbic acid, etc. The amount of use of the polymerization initiator is preferably in the range of 0.001–2 mole percent, more preferably in the range of 0.01–0.5 mole percent.

The absorbing agent in accordance with the present invention is prepared by applying a heat treatment to the precursor of the absorbing agent obtained by the polymerization reaction in a solution so as to have a water content of less than 10 percent and an average particle diameter of 200–600 $\mu$m and a content of particles having a diameter of less than 106 $\mu$m of not more than 10 percent by weight in the presence of a surface crosslinking agent. The resulting precursor of the absorbing agent may have, for example, undefined, globular (spherical), leaflet, granular shape, and the like. Furthermore, the precursor of the absorbing agent may be a primary particle, or a granule of primary particle. In addition, when the water content is above 10 percent, or the average particle diameter is outside the range of 200 $\mu$m–600 $\mu$m, or the ratio of the particle diameter having a diameter of less than 106 $\mu$m is above 10 percent by weight, the absorbing agent having excellent dispersed absorbency under pressure, etc., cannot be achieved.

For the surface crosslinking agent in the present invention, a known surface crosslinking agent is used, and a compound reactive to a carboxyl group is suitable. Examples of such surface crosslinking agent include: polyhydroxy alcohol compounds having at least two hydroxy groups such as ethylene glycol, diethylene glycol, propylene glycol, triethylene glycol, tetraethylene glycol, polyethylene glycol, propylene glycol, 1,3-propanediol, dipropylene glycol, 2,2,4-trimethyl-1,3-pentanediol, polypropylene glycol, glycerol, polyglycerol, 2-butene-1,4-diol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymer, pentaerythritol, sorbitol, etc.; epoxy compounds such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, glycidol, etc.; polyamine compounds such as ethylenediamine, diethylenetriamine, triethylenetetramine, tetraethylenepentamine, pentaethylenehexamine, polyethyleneimine, etc.; polyisocyanate compounds such as 2,4-tolylene diisocyanate, hexamethylene diisocyanate, etc.; polyoxazoline compounds such as 1,2-ethylene bisoxazoline, etc.; alkylene carbonate compounds such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, 1,3-dioxopane-2-one, etc.; haloepoxy compounds such as epichlorohydrin, epibromehydrine, α-methylepichlorohydrin, etc.; a silane coupling agent such as γ-glycidoxypropyltrimethoxysilane, γ-aminopropyltrimethoxysilane, and the like; polyvalent metallic compounds such as hydroxides and chlorides of metals: zinc, calcium, magnesium, aluminum, iron, zirconium, etc. Only one kind of the above-listed surface active agent may be adopted, or two or more kinds thereof may be suitably mixed and adopted.

Especially when the surface crosslinking agent is combined with the first surface crosslinking agent and the second surface crosslinking agent having mutually different solubility parameters (SP value), an absorbing agent with a still improved diffusing absorbency under pressure can be obtained. In addition, the solubility parameter is a value normally used as a factor representing the polarity of the compound. In the present invention, the solubility parameter $\delta$ $(cal/cm^3)^{1/2}$ of the solvent described in pages 527–539 (polymer handbook, the third edition (Wiley Interscience Co., Ltd.)) is applied. As to the solubility parameter of the solvent which is not described in the book, the value obtained by substituting the condensation energy constant of Hoy described on page 525 to the formula of Small described on page 524 of the book can be applied.

For the first surface crosslinking agent, a compound reactive to a carboxylic group having a solubility parameter of more than 12.5 $(cal/cm^3)^{1/2}$ is preferable, and a compound having a solubility parameter of more than 13.0 $(cal/cm^3)^{1/2}$ is more preferable. Examples of the first crosslinking agent include: ethylene glycol, propylene glycol, glycerol, pentaerythritol, sorbitol, ethylene carbonate (1,3dioxorane-2-one), propylene carbonate (4-methyl-1,3dioxorane-2-one), etc. However, the first surface crosslinking agent is not limited to the above example. Only one kind of such first surface crosslinking agent may be used, or more than two kinds thereof may be used.

The second surface crosslinking agent is preferably a compound which is reactive to a carboxyl group, having a solubility parameter of less than 12.5 $(cal/cm^3)^{1/2}$, and more preferably in the range of 9.5–12.0 $(cal/cm^3)^{1/2}$.

Examples of the second surface crosslinking agent include: diethylene glycol, triethylene glycol, tetraethylene glycol, dipropylene glycol, tripropylene glycol, 1,3-butanediol, 1,4-butanediol, 1,5-pentanediol, 2,4-pentanediol, 1,6-hexanediol, 2,5-hexanediol, trimethylolpropane, diethanolamine, triethanolamine, ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, ethylenediamine, diethylenetriamine, triethylene tetramine, 2,4-tolylene diisocyanate, hexamethylene diisocyanate, 4,5-dimethyl-1,3-dioxolane-2-one, epichlorohydrin, epibromohydrin, and the like. The second crosslinking agent of the present invention is not limited to the above-listed compound. Only one kind of such second crosslinking agent may be used, or more than two kinds thereof may be used.

For the surface crosslinking agent of the present invention, a compound of at least one kind selected from the group of the first surface crosslinking agent, and a compound of at least one kind selected from the group of the second surface crosslinking agent may be mixed and used.

Suitable amount of use of the surface crosslinking agent differs depending on a compound to be used, or a combination, etc. However, with respect to 100 parts by weight of solid portion of the precursor of the absorbing agent, the surface crosslinking agent is preferably used in an amount in the range of 0.001–10 parts by weight, and more preferably in the range of 0.01–5 parts by weight. In addition, when the first surface crosslinking agent and the second surface crosslinking agent are used in combination, with respect to 100 parts by weight of the solid portion of the precursor of the absorbing agent, the first surface crosslinking agent is used in a range of 0.01–5 parts by weight, and the second surface crosslinking agent is used in a range between 0.001–1 parts by weight. It is more preferable that the first surface crosslinking agent is used in an amount of 0.1–2 parts by weight, the second surface crosslinking agent is used in the range of 0.005–0.5 part by weight. By using the above surface crosslinking agent, the precursor of the absorbing agent, i.e., the crosslinking density in a vicinity of the surface of the absorbent resin can be increased. When more than 10 parts by weight of the surface crosslinking agent is used, it is not preferable not only for the cost performances, but also in forming the suitable crosslinking structure of the absorbing agent. On the other hand, when less than 0.001 part by weight of surface crosslinking agent is used, it is difficult to obtain an effect of improving the diffusing absorbency under pressure of the absorbing agent. Therefore, such condition is not preferable.

When mixing the precursor of the absorbing agent with the surface crosslinking agent, it is preferable to use water as a solvent. The amount of use of water differs depending on the kinds, particle diameter, water content, etc., of the precursor of the absorbing agent. However, the amount of use of water is preferably above 0 and less than 20 parts by weight, more preferably in the range of 0.5–10 parts by weight, with respect to 100 parts by weight of the solid portion of the precursor of the absorbing agent.

When mixing the precursor of the absorbing agent with the surface crosslinking agent, a hydrophilic organic solvent may be used as a solvent if necessary. Examples of such hydrophilic organic solvent include: lower alcohol such as methyl alcohol, ethyl alcohol, n-propyl alcohol, isopropyl alcohol, n-butyl alcohol, isobutyl alcohol, t-butyl alcohol, etc.; ketone such as acetone, etc.; ether such as dioxane, tetrahydrofuran, etc.; amide such as N,N-dimethyl formamide, etc., sulfoxide such as dimethylsulfoxide, etc. Suitable amount of use of the hydrophilic organic solvent varies depending on kinds, particle diameter and water content of the precursor of the absorbing agent. However, the content of the hydrophilic organic solvent is preferably not more than 20 parts by weight, more preferably in a range of from 0.1–10 parts by weight of 100 parts of the solid portion of the precursor of the absorbing agent.

Then, when mixing the precursor of the absorbing agent with the surface crosslinking agent, for example, after dispersing the precursor of the absorbing agent in the hydrophilic organic solvent, the surface crosslinking agent may be mixed. However, the mixing method is not especially limited. Among various mixing processes, the process wherein the surface crosslinking agent which is dissolved in water and/or hydrophilic organic solvent, when an occasion demands, is mixed with the precursor of the absorbing agent directly or by spraying or dropping it is preferable. When mixing with water, fine particles undissolvable in water or the surface active agent, etc., may be used in combination.

The mixer for use in mixing the precursor of the absorbing agent with the surface crosslinking agent preferably has a strong mixing force so that both can be mixed homogeneously and surely. Examples of such mixer include: a cylindrical mixer, a double wall conical mixer, V-shaped mixer, ribbon type mixer, screw-type mixer, flow-type oven rotary disk mixer, air-flow type mixer, two-arm type kneader, internal mixer, grinding kneader, rotary mixer, screw type extruder, etc.

After mixing the precursor of the absorbing agent with the surface crosslinking agent, a heat treatment is applied so as to crosslink around the surface of the precursor of the absorbing agent. Suitable temperature of applying the heat treatment varies depending on the surface crosslinking agent to be used. However, it is preferably in the range between 80° C. and 250° C., more preferably in the range between 120° C. and 230° C. When using the first surface crosslinking agent and the second surface crosslinking agent in combination, the heat treatment is suitably applied at a temperature not less than 160° C. When the heat treatment is applied at temperature below 80° C. (below 160° C. when using both the first and second surface crosslinking agents), a uniform crosslinking structure is not formed. Therefore, the absorbent resin having excellent properties such as diffusing absorbency under pressure, etc., cannot be obtained. Therefore, such condition is not preferable. Besides, as it takes a long time for applying the heat treatment, the productivity is low. On the other hand, when the heat treatment is applied at above 250° C., properties of the precursor of the absorbing agent are lowered, which results in poor performances of the absorbing agent. Thus, such condition is not preferable.

The described heat treatment may be applied using general dryer, heating oven, etc. Examples of such dryer include: groove type mixing dryer, rotary dryer, disk dryer, fluidized layer dryer, air-flow type dryer, infrared radiation dryer, etc.

The absorbing agent resulting from the described manufacturing process has a diffusing absorbency under pressure of about 25 g/g when 60 minutes has elapsed after the absorption started, and a water soluble content in the range between 0 percent by weight and 7 percent by weight. Therefore, the absorbing agent has described excellent absorbing properties. The reason why the absorbing agent of the present invention shows excellent performances in its diffusing absorbency under pressure, etc., is not specified. However, it can be estimated that by using the dispersant as well as a specific amount of the crosslinking agent prepared so as to have a specific range of high-boiling point component, the high-boiling point component is homogeneously dispersed in the reaction system, and the crosslinking ability of the main component thereof disturbed by the high-boiling point component can be fully exhibited. In the meantime, the crosslinking reaction by the high-boiling point component can be performed effectively. As a result, the content of the water-soluble component can be significantly reduced.

The described absorbing agent is provided with excellent absorbing properties. Therefore, in the case of applying the absorbing agent to an absorbent material, for example, sanitary goods such as a paper diaper, sanitary napkin, incontinence pad, etc., even when the resin concentration in the absorbent material is high, such excellent properties that high diffusing absorbency under pressure, and low water soluble content can be obtained irrespectively of the structure of the absorbent material. In addition, such sanitary goods have small amount of wet back after a long period of time, very high liquid diffusivity, and a stability of keeping the amount of water for a long period of time, thereby providing an absorbent product which shows excellent performances. Such absorbing agent can be suitably used, especially in sanitary goods, such as paper diaper, sanitary napkin, a so-called incontinence pad, and the like, to meet the demand of higher performances and thinner type thereof. Thus, the described process enables the absorbing agent which shows excellent properties to be manufactured.

In addition, deodorant, perfume, inorganic powder, foaming agent, pigment, dye, hydrophilic short fiber, synthetic fiber, fertilizer, oxidizing agent, reducing agent, water, salts, etc., may be added to the resulting absorbing agent and the absorbent material prepared by the process of the present invention, which enables the absorbing agent, absorbent material and absorbent product to have various functions.

Next, the absorbing agent, the absorbent material and the absorbent product which show excellent properties (absorbing properties) such as high liquid diffusivity and water absorbency under pressure, etc., even if the resin concentration is raised will be explained.

The absorbent material of the present invention includes at least 40 percent by weight of the absorbing agent having the diffusing absorbency under pressure of at least 25 g/g when 60 minutes has elapsed after the absorption is started, preferably 50 percent by weight, more preferably 60 percent by weight, and most preferably 70 percent by weight. The absorbing agent having the diffusing absorbency under pressure of at least 25 g/g measured when 60 minutes has elapsed after the absorption is started is unpreferable because the liquid diffusivity in the lateral direction in the absorbent material (high concentration) having an increased resin concentration is lowered, and the absorbing capacity of the absorbent material becomes small. It is preferable that the diffusing absorbency under pressure after 60 minutes elapsed is not less than 30 g/g. In addition, even when the absorbing agent having the diffusing absorbency under pressure of not less than 25 g/g is included, per unit absorbing capacity of the absorbent material having the ratio of absorbing agent of less than 40 percent by weight would be lowered. In the absorbent material of the present invention, in addition to the diffusing absorbency under pressure, when 60 minutes has elapsed after the absorption is started, it is preferable to include the absorbing agent having the diffusing absorbency under pressure of 15 g/g computed based on the value measured when 30 minutes has elapsed after the absorption is started. Furthermore, it is most preferable to include the absorbing agent having the diffusing absorbency under pressure of at least 15 g/g computed based on the value measured when 20 minutes has elapsed after the absorption is started.

Namely, it is preferable that the absorbing agent of the present invention has the diffusing absorbency under pressure of not less than 15 g/g when 30 minutes has elapsed after the absorption is started and the diffusing absorbency under pressure of not less than 25 g/g when 60 minutes has elapsed. It is more preferable that the diffusing absorbency under pressure is not less than 15 g/g when 20 minutes has elapsed after the absorption is started, and the diffusing absorbency under pressure measured when 60 minutes has elapsed after the absorption is started is not less than 25 g/g. It is the most preferable that the diffusing absorbency under pressure measured when 60 minutes has elapsed is not less than 15 g/g, and the diffusing absorbency under pressure measured when 60 minutes has elapsed is not less than 30 g/g. The absorbing agent has the diffusing absorbency under pressure of less than 15 g/g when 30 minutes has elapsed after the absorption is started is unpreferable because the liquid diffusivity in lateral direction would be deteriorated, and the absorbing force of the absorbent material is lowered.

Other than the absorbing agent, the absorbent material in accordance with the present invention may include the hydrophilic fiber if necessary. The structure of the absorbent material may be the aforementioned structure, but is not especially limited. However, it is preferable that the absorbing agent and the hydrophilic fiber are homogeneously mixed so as to have the ratio of the absorbing agent in the absorbent material not less than 40 percent by weight. It is still more preferable that the absorbing agent and the hydrophilic fiber are uniformly mixed so as to have the absorbing agent used in an amount not less than 50 percent by weight, preferably 60 percent by weight, more preferably 70 percent by weight with respect to the total amount of the absorbing agent and the hydrophilic agent. By the described arrangement, the absorbent material can fully exhibit the absorbing properties. In addition, the higher is the resin concentration in the absorbent material, the more obvious are the properties of the absorbing agent and the absorbent material of the present invention.

In the case where the ratio of the hydrophilic fiber in the absorbent material is relatively small, absorbent materials, i.e., hydrophilic fibers may be linked to one another using the described adhesive binder.

The absorbing agent of the present invention is obtained by first synthesizing the precursor of the absorbing agent and then applying the heat treatment to the precursor of the absorbing agent in the presence of a specific surface crosslinking agent. The precursor of the absorbing agent has an average particle diameter in the range of 200–600 $\mu$m, and includes 10 percent by weight of particles having a particle diameter of 106 $\mu$m. Such precursor of the absorbing agent is a resin for use in forming hydrogel by absorbing a large amount of water. For example, the precursor of the absorbing agent is synthesized by the aqueous solution polymerization. Examples of the precursor of the absorbing agent include: a partially neutralized crosslinked polymer of polyacrylic acid, a hydrolyzed graft polymer of starch-acrylonitrile, a neutralized graft polymer of starch-acrylic acid, a saponified copolymer of vinyl acetate-acrylic ester, a hydrolyzed copolymer of acrylonitrile or of acrylamide, or a crosslinked polymer thereof, crosslinked denatured polyvinyl alcohol containing carboxyl group, a copolymer of crosslinked isobutylene maleic anhydride, and the like.

The precursor of the absorbing agent may be obtained by performing a polymerization or a copolymerization of at least one kind selected from unsaturated carboxylic acid such as (meth)acrylic acid, maleic acid, maleic anhydride, fumaric acid, crotonic acid, itaconic acid, β-acryloxypropionic acid or the above acids in a neutralized form, and further pulverizing or classifying the polymer, if necessary, to have the above-defined particle diameter. Among the above-listed monomers, (meth)acrylic acid and neutralized form thereof are especially preferable.

The precursor of the absorbing agent may be a copolymer of the monomer and the other monomer which is copolymerizable with the monomer. Examples of the other monomer include: the exemplified unsaturated monomer, i.e., the anionic unsaturated monomer and salts thereof; a nonionic unsaturated monomer having a hydrophilic group; a cationic unsaturated monomer, etc.

The precursor of the absorbing agent includes a carboxyl group. The amount of the included carboxyl group in the precursor is not especially limited. However, it is preferable that the carboxyl group of not less than 0.01 equivalent value exists with respect to 100 g of the precursor of the absorbing agent. When the precursor of the absorbing agent is, for example, a crosslinked polymer of partially neutralized polyacrylic acid, it is preferable that the ratio of unneutralized polyacrylic acid in the crosslinked compound is in the range of 1–60 mole percent, more preferably 10–50 mole percent.

It is preferable that the inside of the precursor of the absorbing agent is crosslinked by reacting or copolymerizing with the crosslinking agent including plural polymerizable unsaturated groups and plural reactive groups. The precursor of the absorbing agent may be the self crosslinkable type which does not require the crosslinking agent. Examples of such crosslinking agent include: N,N'-methylenebis(meth)acrylamide, (poly)ethylene glycol di(meth)acrylate, (poly)propylene glycol di(meth)acrylate, trimethylolpropane di(meth)acrylate, trimethylolpropane tri(meth)acrylate, glycerol tri(meth)acrylate, glycerin acrylate methacrylate, ethylene oxide denatured trimethylolpropane tri(meth)acrylate, pentaerythritol tetra(meth)acrylate, dipentaerythritol hexa(meth)acrylate, triallyl cyanurate, triallyl isocyanurate, triallylphosphate, triallylamine, poly(meth) aryloxyalkane, (poly)ethylene glycol diglycidyl ether, glycerol diglycidyl ether, ethylene glycol, polyethylene glycol, propylene glycol, glycerol, pentaerythritol, ethylenediamine, polyethyleneimine, glycidyl(meth) acrylate, etc. Only one kind of the above-listed crosslinking agent may be adopted, or two or more kinds thereof may be suitably mixed and adopted. Among the above-listed compounds, it is preferable to use the compound including plural polymerizable unsaturated groups as a crosslinking agent.

It is preferable that the crosslinking agent is used in an amount in the range of 0.005–2 mole percent, more preferably in the range of 0.05–1 mole percent. If the amount of use of the crosslinking agent is less than 0.005 mole percent or more than 2 mole percent, the diffusing absorbency under pressure of the absorbing agent will be lowered Thus, such condition is unpreferable.

For the polymerization initiation in the polymerization reaction, the above-exemplified radical polymerization initiator, or the active energy ray, etc., may be used.

The described precursor of the absorbing agent does not have the diffusing absorbency under pressure in the preferable range of the present invention. Therefore, it is required to set the crosslinked density in a vicinity of the surface of the precursor of the absorbing agent higher than the inside thereof by adopting the surface crosslinking agent. Namely, by crosslinking around the surface of the precursor of the absorbing agent using a specific surface crosslinking agent, the absorbing agent of the present invention can be achieved.

The absorbing agent in accordance with the present invention is prepared by adjusting the precursor of the absorbing agent obtained by the aqueous solution polymerization so as to have an average particle diameter of 200–600 μm, and not more than 10 percent by weight of the particle diameter below 106 μm by classification, etc., and thereafter applying a heat treatment to the precursor of the absorbing agent in the presence of the specific surface crosslinking agent. The precursor of the absorbing agent may be formed in granules of the defined shape or in the shape of undefined, granular, leaflet, granular, etc. Furthermore, the precursor of the absorbing agent may be a primary particle, or a granule of primary particles. In addition, in the case where the average particle diameter is outside the range of 200–600 μm, and the case where the ratio of the particles having a diameter of 106 μm is above 10 percent by weight, absorbing agents having excellent properties such as diffusing absorbency under pressure, etc., cannot be obtained.

The surface crosslinking agent is a combination of the first surface crosslinking agent and the second crosslinking agent having mutually different solubility parameters (SP value). Thus, it is preferable that a compound of at least one kind selected from the group of the first surface crosslinking agent and a compound of at least one kind selected from the group of the second surface crosslinking agent are mixed and used. In the case of adopting only the first surface crosslinking agent of at least one kind, or the second surface crosslinking agent of at least one kind, it may be difficult to obtain the absorbing agent having excellent performances of the diffusing absorbency under pressure, etc.

For the amount of use of the surface crosslinking agent, and the method of mixing the precursor of the absorbing agent with the surface crosslinking agent, the previously described amount of use, the mixing method, the mixer, etc., may be used. In addition, in the case of mixing the precursor of the absorbing agent with the surface crosslinking agent, the previously described solvent (water and/or hydrophilic organic solvent) may be used.

Suitable temperature of applying the heat treatment varies depending on the surface crosslinking agent. However, it is preferably in the range of 160° C. to 250° C. When the heat treatment is applied at a temperature below 160° C., a homogeneous crosslinking structure may not be formed, and an absorbing agent having excellent performances in its diffusing absorbency under pressure, etc., cannot be obtained. Therefore, such condition is not preferable. In addition, since a long time is required for applying the heat treatment, a productivity would be lowered. On the other hand, when applying the heat treatment at a temperature above 250° C., the properties of the precursor of the absorbing agent are lowered, and the performances of the absorbing agent are poor. Therefore, such condition is also not preferable. The described heat treatment is performed using the exemplified dryer or a heat oven.

The absorbing agent resulting from the described process has 15 g/g of diffusing absorbency under pressure measured when 30 minutes has elapsed after the absorption is started, and a diffusing absorbency under pressure of 25 g/g after 60 minutes elapsed. As described, the absorbent material contains such absorbing agent in an amount of not less than 40 percent by weight. Therefore, the absorbing agent and the absorbent material show described excellent absorbing properties. Therefore, for example, in the case where it is used in the absorbent product, the absorbent material can provide the excellent properties such as high liquid diffusivity, water retaining property, etc., even in the case of using a large amount of absorbing agent or using the absorbent material having high resin concentration.

The reason why the absorbent material using the absorbing agent of the present invention shows excellent performances in its diffusing absorbency under pressure, etc., is not clear. However, it can be assumed that in the conventional absorbent material, the liquid diffusion and the liquid transmission of the aqueous liquid in the absorbent material is performed by capillarity of hydrophilic fiber, whereas in the absorbent material of the present invention, precise liquid diffusivity (liquid diffusing ability and liquid transmitting ability) which the absorbing agent having excellent diffusing absorbency under pressure has can be fully achieved even in the absorbent material.

The absorbent product in accordance with the present invention includes an absorbing layer including the absorbent material having the described structure which is sandwiched between a liquid permeable sheet and an impermeable sheet. Since the absorbent product is provided with the absorbing layer including the absorbent material having the described arrangement, the above-mentioned excellent water absorbing properties can be achieved. Examples of the absorbent product include: sanitary goods such as paper diaper, sanitary napkin, incontinence pad, etc. However, the present invention is not limited to the above-listed absorbent products. Since the absorbent product of the present invention has excellent absorbing properties, in its application of paper diaper, etc., the leakage of urea can be prevented, and thus the paper diaper can be maintained dry.

A sheet which is permeable to liquid (hereinafter referred to as a liquid permeable sheet) is composed of a material which is transmissive to aqueous liquid. For the material of the liquid permeable sheet, nonwoven fabric, woven fabric; a porous synthetic resin film such as polyethylene, polypropylene, polyester, polyamide, etc., may be used. The sheet which is impermeable to liquid (hereinafter referred to as liquid impermeable sheet) is made of a material having properties that aqueous liquid is not transmitted. For the material of the liquid impermeable sheet, for example, a synthetic resin film such as polyethylene, polypropylene, ethylenevinylacetate, polyvinyl chloride; a film composed of the above-mentioned synthetic resin and nonwoven fabric, a film composed of the synthetic material of synthetic resin and woven fabric, etc., may be used. In addition, a liquid impermeable sheet may have property of transmitting vapor.

The arrangement of the absorbing layer is not particularly limited, as long as the described absorbent material is included. Similarly, the method of manufacturing the absorbing layer is not especially limited. Furthermore, the method of sandwiching the absorbing layer between the liquid permeable sheet and the liquid impermeable sheet, and the method of manufacturing the absorbent product are not especially limited.

In addition, deodorant, perfume, inorganic powder, foaming agent, pigment, dye, hydrophilic short fiber, synthetic fiber, fertilizer, oxidizing agent, reducing agent, water, salts, etc., may be added to the resulting absorbing agent, absorbent material or absorbent product prepared by the process of the present invention, which enables them to have various functions.

For a fuller understanding of the nature and advantages of the invention, reference should be made to the ensuing detailed description taken in conjunction with the accompanying drawings.

DESCRIPTION OF THE PREFERRED EMBODIMENTS

Figure 1:
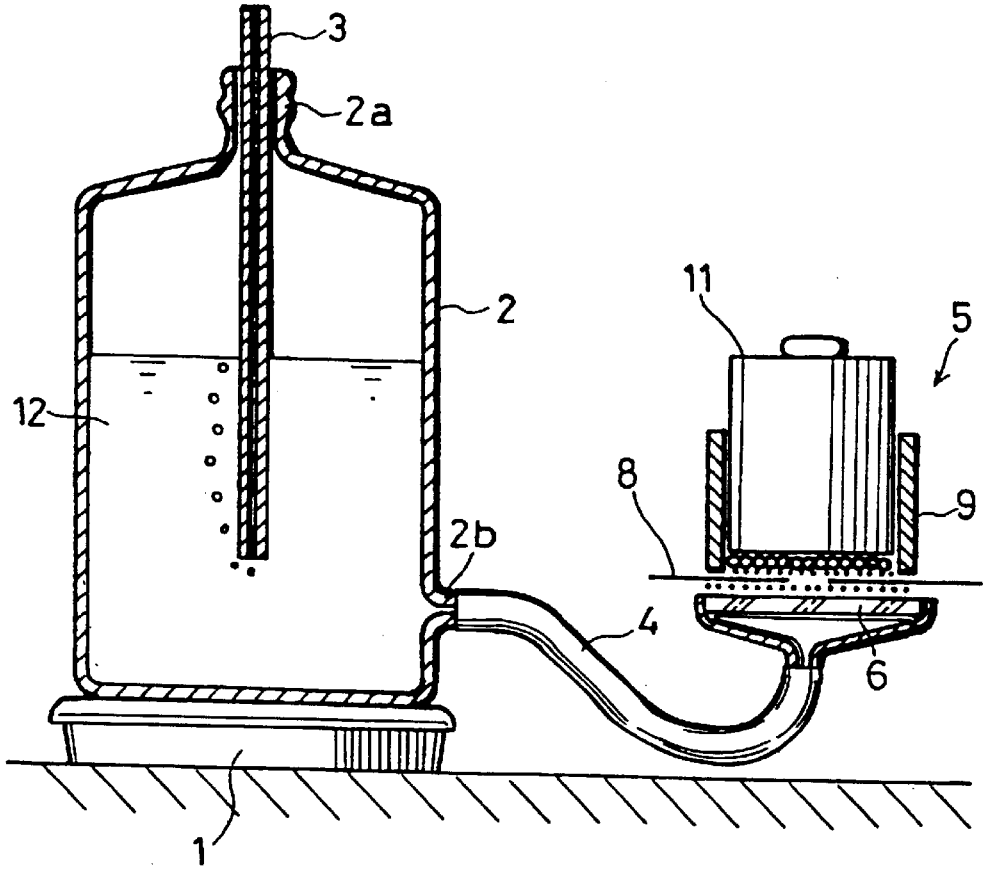
FIG. 1 is a schematic cross-sectional view of a device of measuring a diffusing absorbency under pressure as one of the properties of an absorbing agent of the present invention.

Hereinafter, this invention is illustrated by the following examples of some preferred embodiments in comparison with comparative examples not according to the invention. However, this invention is not limited to the undermentioned examples. Evaluation methods of properties of absorbing agents, absorbent materials, and absorbent products performed in the examples and comparative examples are as follows.

(a) Absorbency under pressure i) tea bag method 0.2 gram of the absorbing agent (precursor of the absorbing agent) was uniformly placed into a bag like a tea-bag (40 mm×150 mm) made of nonwoven fabric, and was immersed into a solution of 0.9 percent by weight of sodium chloride (physiological saline solution). After leaving it for 60 minutes, the bag was taken out. Then, the bag was subjected to hydro-extraction for a predetermined period of time, and the weight $W_{1a}$ (g) of the bag was measured. Further, the same processes are carried out without using the absorbing agent, and the weight $W_{0a}$ (g) of the bag was measured. The absorbency under pressure (g/g) was calculated from the weights $W_{1a}$ and $W_{0a}$ in accordance with the following equation:

Absorbency under pressure (g/g)=(Weight $W_{1a}$(g)−Weight $W_{0a}$(g))/Weight of Absorbing Agent (g)

ii) centrifugal separation method 0.2 gram of the absorbing agent was uniformly placed into a bag (60 mm×60 mm) made of nonwoven fabric, and was immersed into a solution of sodium chloride of 0.9 percent by weight (physiological saline solution). After leaving it for 60 minutes, the bag was taken out. Then, the bag was subjected to hydroextraction for 3 minutes at 250 G using a centrifugal separator, the weight $W_{1b}$ (g) of the bag was measured. Further, the same processes are carried out without using the absorbent resins, and the weight $W_{0b}$ (g) of the bag was measured. The absorbency under pressure (g/g) was calculated from the weights $W_{1b}$ and $W_{0b}$ from the following equation:

Absorbency under pressure (g/g)=(Weight $W_{1b}$(g)−Weight $W_{0b}$(g))/Weight of Absorbing agent (g).

(b) water soluble component content

In 1000 ml of deionized water, 0.500 g of absorbing agent (precursor of the absorbing agent) was diffused, and after agitating it for 16 hours, the mixture was filtered off through a filter paper. Next, 50 g of the resulting filtrate was collected in a 100 ml beaker. To the filtrate were added 1 ml of 0.1N sodium hydroxide solution, 10.00 ml of N/200 methylglycol chitosan solution and 4 drops of 0.1 percent toluidine blue solution. Thereafter, the solution in the beaker was colloidal-titrated by a solution of N/400 potassium polyvinyl sulfate. When the solution changed its color from blue to red purple, it was determined that the titration was completed, and the amount of titration A (ml) was calculated. Further, the same processes were carried out using 50 g of deionized water in place of 50 g of filtrate, and the amount of titration B (ml) was calculated as blank titration. The water soluble component content was calculated from amount of titration A and B, and neutralization×(mole percent) of acrylic acid added to the absorbing agent in accordance with the following equation.

Water soluble component content (percent by weight)=(B (ml)−A (ml))×0.01×[72·(100−x)+94x]/100

(c) Diffusing Absorbency under pressure of the Absorbing Agent

First, the device used in measuring the diffusing absorbency under pressure of the absorbing agent will be briefly explained below in reference to FIG. 1 and FIG. 2.

As shown in FIG. 1, the measuring device includes a balance 1, a container 2 placed on the balance 1 of a predetermined capacity, an air-intake pipe 3, a conduit 4, a glass filter 6, and a measuring section 5 that is placed on the glass filter 6. The container 2 has an opening 2a on its top portion and an opening 2b on its side portion, and the air-intake pipe 3 is inserted through the opening 2a while the conduit 4 is fixed to the opening 2b. Further, a predetermined amount of physiological saline solution 12 is placed in the container 2. The lower end portion of the air-intake pipe 3 is dipped into the physiological saline solution 12. The glass filter 6 has a diameter of 70 mm. The container 2 and the glass filter 6 are connected to each other through the conduit 4. The glass filter 6 is fixed at a position slightly above the lower end of the air-intake pipe 3.

Figure 2:
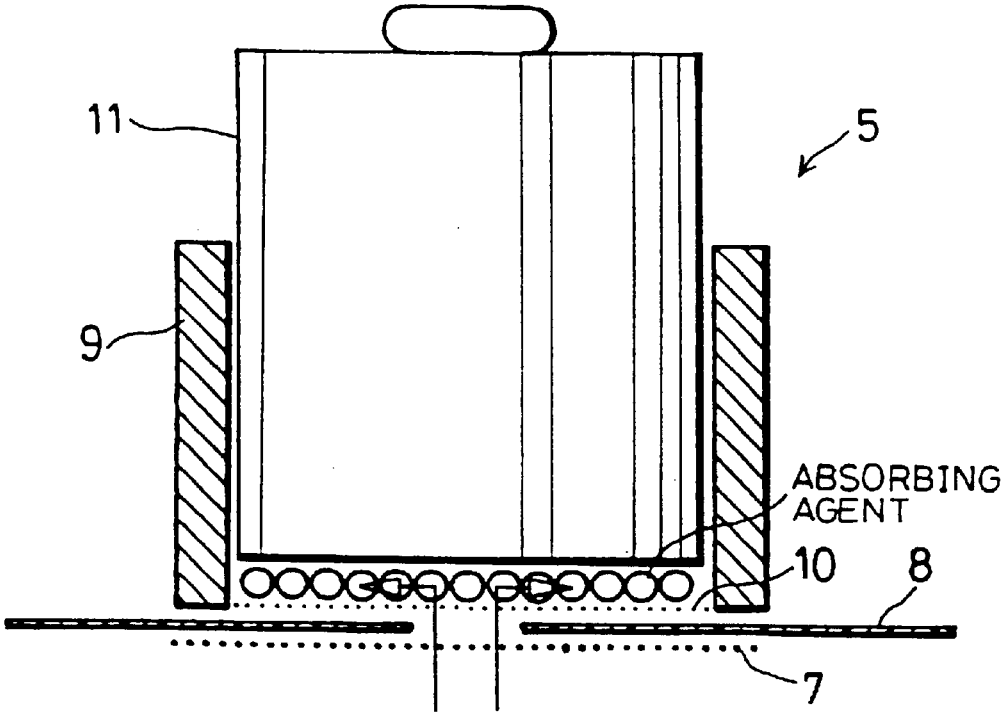
FIG. 2 is a schematic cross-sectional view showing an essential part of the measuring device of FIG. 1.

As shown in FIG. 2, the measuring section 5 is provided with a paper filter 7, a sheet 8, a supporting cylinder 9, a metal gauze 10 that is affixed to the bottom of the supporting cylinder 9, and a weight 11. In the measuring section 5, the paper filter 7, the sheet 8, and the supporting cylinder 9 (that is, the metal gauze 10) are placed on the glass filter 6 in this order, and the weight 11 is placed on the metal gauze 10 inside the supporting cylinder 9. The sheet 8 is made of polyethylene terephthalate (PET) and is formed in a doughnut shape with a thickness of 0.1 mm having an opening at a center with a diameter of 18 mm. The supporting cylinder 9 has an inner diameter of 60 mm.

The metal gauze 10, made of stainless steel, is designed to be 400-mesh (the size of each mesh: 38 $\mu$m). Thus, a predetermined amount of the absorbing agent is uniformly scattered on the metal gauze 10. The weight 11 is adjusted so that it can uniformly apply a load of 20 g/cm$^2$ to the metal gauze 10, that is, to the absorbing agent.

The diffusing absorbency under pressure of the absorbing agent was measured by using the measuring device having the above-mentioned arrangement. The following description will discuss the measuring method.

First, predetermined preparatory operations were carried out, such as a predetermined amount of physiological saline solution 12 was put into the container 2; the air-intake pipe 3 was inserted into the container 2; and other preparatory operations were performed. Next, the paper filter 7 was placed onto the glass filter 6. The sheet 8 was placed on the paper filter 7 in such a manner that its opening was positioned at the center of the glass filter 6. In the meantime, 1.5 g of the absorbent resins (preferably, the absorbent resin prepared so as to have a particle diameter of 300–500 $\mu$m by classification, etc.) was uniformly scattered on the metal gauze 10 inside the supporting cylinder 9, and the weight 11 was placed on the absorbing agent.

Successively, the metal gauze 10, that is, the supporting cylinder 9 whereon the absorbing agent and the weight 11 were placed, was placed on the sheet 8, in such a manner that the center of the supporting cylinder 9 coincides with the center of the glass filter 6.

Figure 3:
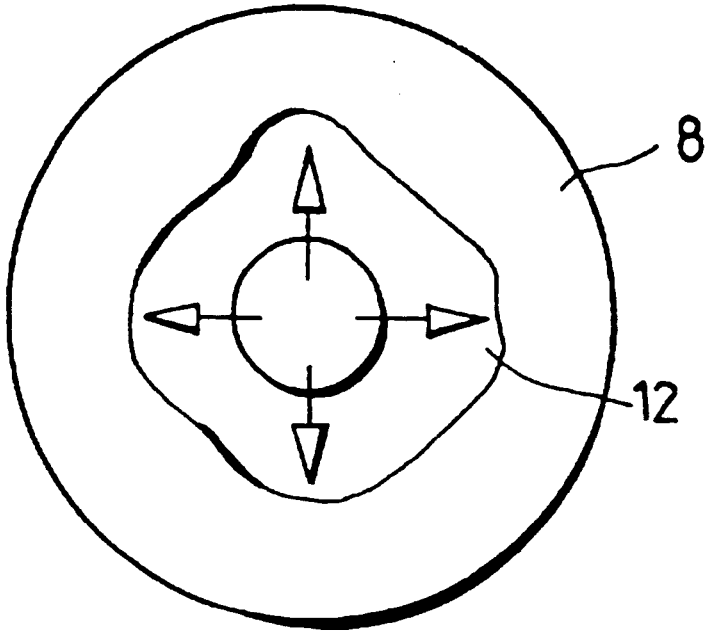
FIG. 3 is an explanatory view showing a diffusing direction of physiological saline solution.

Then, the weight $W_2$(g) of the physiological saline solution 12, which had been absorbed by the absorbing agent for 20, 30 or 60 minutes from the time when the supporting cylinder 9 was placed on the sheet 8 was measured by the balance 1. Further, as shown in FIG. 3, after passing through the opening of the sheet 8, the physiological saline solution 12 was absorbed by the absorbing agent while being uniformly diffused in a lateral direction.

The diffusing absorbency under pressure (g/g) of the absorbing agent when 20, 30 and 60 minutes has elapsed after the absorption was started was calculated from the following equation:

Diffused Absorbing ratio of the Absorbing agent (g/g)= Weight $W_2$(g)/Weight (g) of the Absorbing agent (g).

(d) Absorbency under Pressure of the Absorbing Agent

Figure 4:
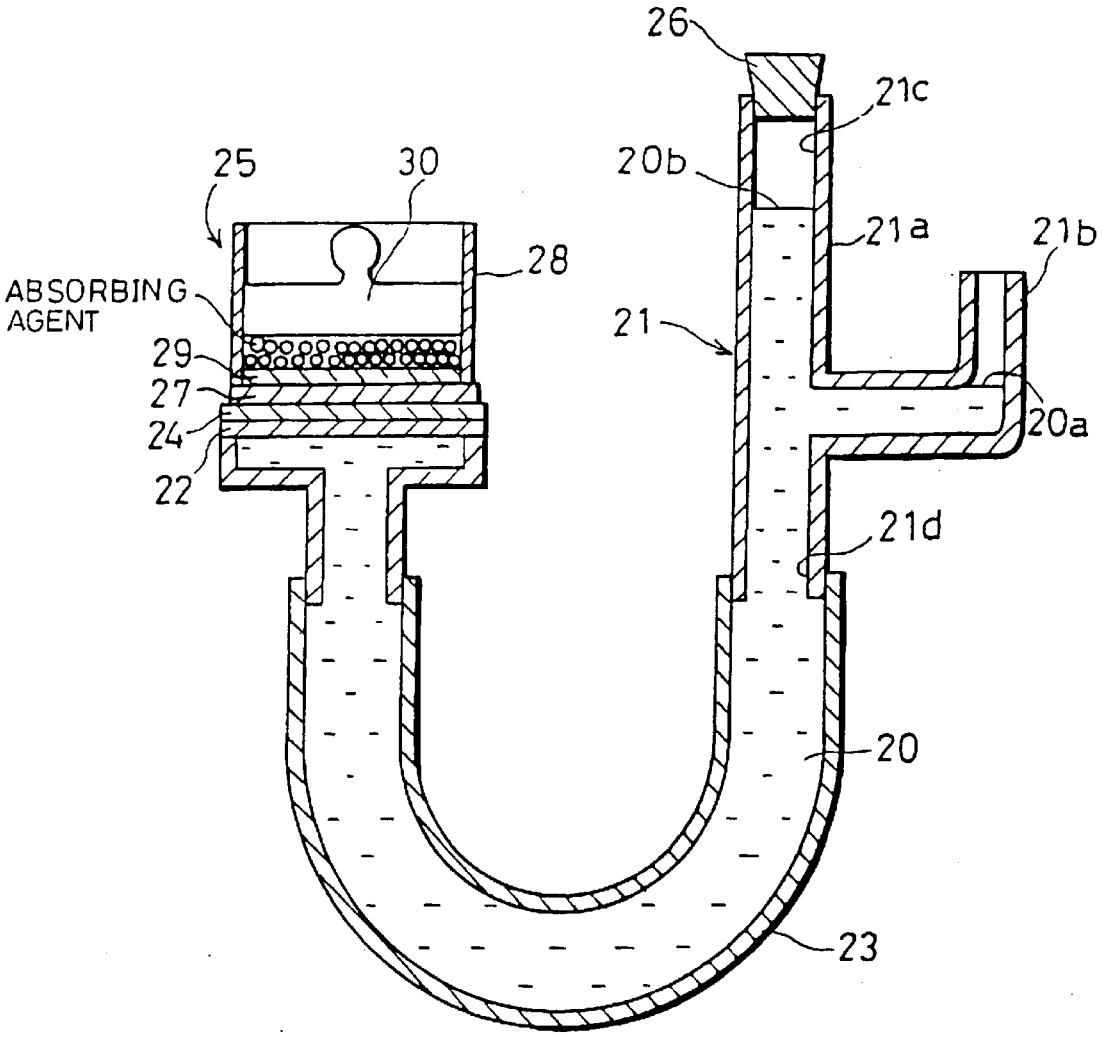
FIG. 4 is a schematic crosssectional view of a device of measuring a water absorbency under pressure as one of the properties of the absorbing agent of the present invention.

First, the device used in measuring the absorbency under pressure of the absorbing agent will be briefly explained in reference to FIG. 4.

As shown in FIG. 4, the measuring device includes a buret 21, a measuring plate 22, a conduit 23, a glass filter 24 placed on the measuring plate 22, and a measuring section 25 placed on the glass filter 24. The buret 21 is formed in substantially T-shape and includes a main conduit 21a and side conduits 21b. The main conduit 21a has an opening 21c on its top portion and an opening 21d at its bottom portion, and a stopcock 26 is fitted to the opening 21c, while the conduit 23 is mounted to the opening 21d. In addition, the side conduit 21b is projected at a center on the side face of the main conduit 21a, and the leading end thereof has an opening in an upward direction. The measuring plate 22 has an upper surface with a diameter of 70 mm. The buret 21 and the measuring plate 22 are connected through the conduit 23. In the buret 21, the measuring plate 22, and the conduit 23, i.e., a continuous portion, a predetermined amount of artificial urea 20 is placed. The main conduit 21a of the buret 21 has a scale. In the buret 21, the position of the liquid face 20a in the side conduit 21b has a predetermined height position below the liquid face 20b of the main conduit 21a.

The measuring section 25 includes a filter paper 27, a supporting cylinder 28, a nonwoven fabric 29 laminated on the bottom portion of the supporting cylinder 28 and a weight 30. The measuring section 25 is arranged such that the filter paper 27, and the supporting cylinder 28 (nonwoven fabric 29) are placed in this order on the glass filter 24, and the weight 30 is placed in the supporting cylinder 28, i.e., on the nonwoven fabric 29. The glass filter 24 is formed so as to have a diameter of 70 mm. The supporting cylinder 28 has an inner diameter of 55 mm. When placing the measuring section 25, the position of the filter paper 27 is set at the same position as the liquid face 20a of the side conduits 21b. Then, a predetermined amount of the absorbing agent is uniformly dispersed on the nonwoven fabric 29. The weight 30 is adjusted so as to uniformly apply a load of 20 g/cm$^2$, to the nonwoven fabric 29, that is, to the absorbing agent.

Using the measuring device of the described arrangement, the absorbency under pressure of the absorbing agent was measured in the following manner.

First, a predetermined amount of artificial urea 20 (composition: 1.9 percent by weight of urea, 0.8 percent by weight of NaCl, 0.1 percent by weight of $CaCl_2$, and 0.1 percent by weight of $MgSO_4$) was prepared, and was poured in the above-mentioned connected portion. Then, the opening 21c of the buret 21 was closed with the stopcock 26, and a predetermined preparatory operation was performed such as placing the measuring plate 22 at a predetermined height position. Then, the filter paper 27 was placed on the glass filter 24 provided at the central portion of the measuring device 22. In the meantime, 0.20 g of the absorbing agent was uniformly diffused in the inside of the supporting cylinder 28, i.e., on the nonwoven fabric 29, and the weight 30 was placed on the absorbing agent.

Then, on the filter paper 27, the nonwoven fabric 29, i.e., the supporting cylinder 28 for storing therein the absorbing agent and the weight 30, was placed in such a manner that the center thereof coincided with the center of the glass filter 24.

After placing the supporting cylinder 28 on the filter paper 27, a volume $V_1$ (ml) of the artificial urea 20 absorbed by the absorbing agent in 30 minutes was measured by reading the scale of the buret 21. Then, from the obtained volume $V_1$, the absorbency under pressure (ml/g) of the absorbing agent measured when 30 minutes has elapsed after the absorption was started from the following formula:

Absorbency under pressure of the absorbing agent (ml/g)=volume $V_1$ (ml)/weight of the absorbing agent (g).

(e) Diffusing absorbency under Pressure of the Absorbent Product (Absorbent Material)

Figure 5:
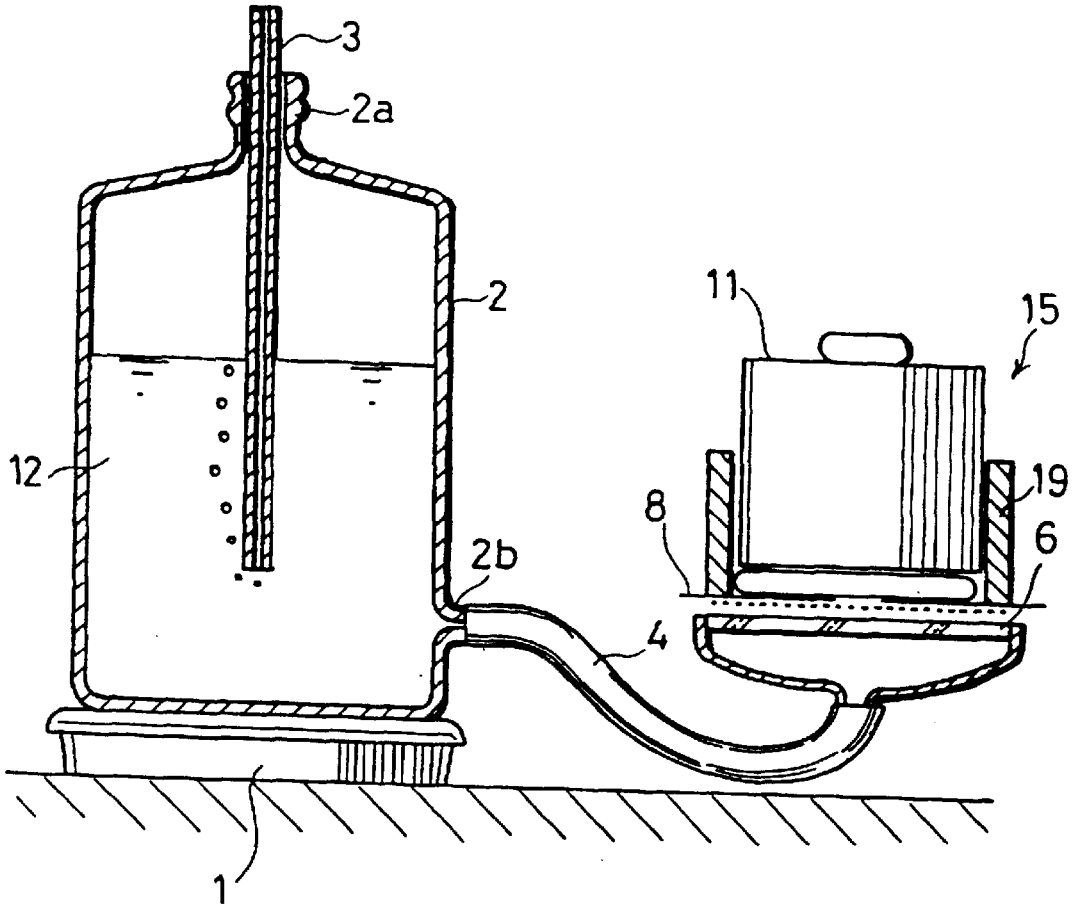
FIG. 5 is a cross-sectional view of the device of measuring the diffusing absorbency under pressure as one of the properties of the absorbent product or the absorbent material of the present invention.
Figure 6:
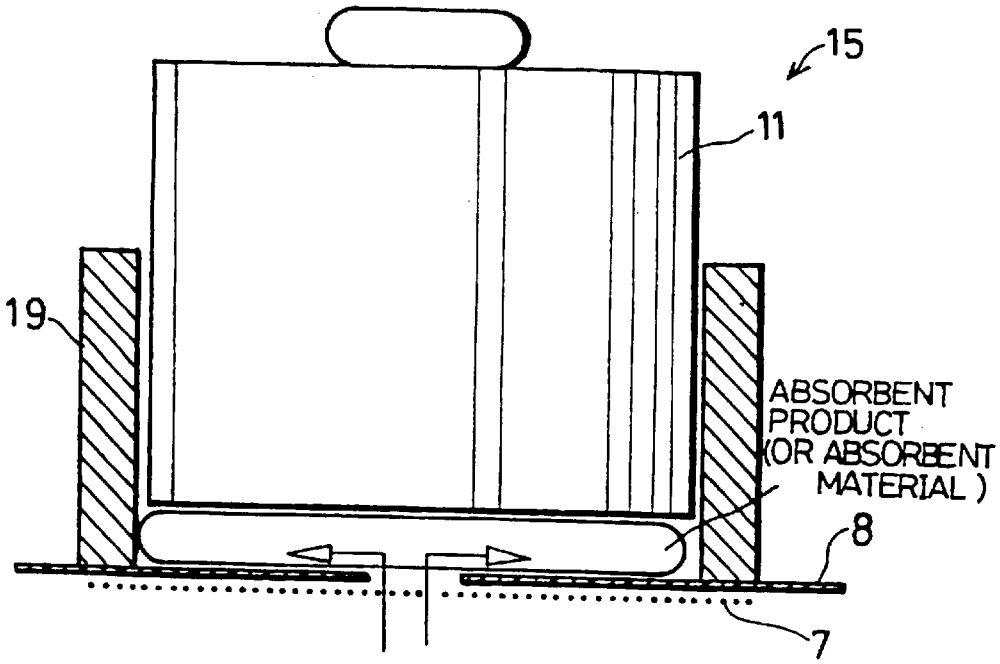
FIG. 6 is a cross-sectional view showing an essential part of the measuring device of FIG. 5.

First, the device of measuring the diffusing absorbency under pressure of the absorbent product (or absorbent material, for convenience, both absorbent material and the absorbent product are simply referred to as an absorbent product) will be briefly explained in reference to FIG. 5 and FIG. 6. For convenience in explanation, members having the same functions as the aforementioned device used in measuring the diffusing absorbency under pressure will be designated by the same reference numerals, and thus the descriptions thereof shall be omitted here.

As described in FIG. 5, the measuring device includes: a balance 1, a container 2, an air-intake pipe 3, a conduit 4, and a glass filter 6 having a diameter of 120 mm, and a measuring section 15 placed on the glass filter 6. As shown in FIG. 6, the measuring section 15 includes a filter paper 7, a sheet 8, an angular supporting cylinder 19 and a weight 11. The described metal gauze is not provided.

The measuring section 15 includes the filter paper 7, the sheet 8 and the angular supporting cylinder 19 which are placed on the glass filter 6 in this order and the weight 11 placed on the inside of the angular supporting cylinder 19. The sheet 8 is made of polyethylene terephthalate, and is formed in a rectangular shape with an opening with a size of 12.5 mm×100 mm at the center and a thickness of 0.1 mm. The angular supporting cylinder 19 is formed so as to have an inner size of 100 mm×100 mm. Further, a predetermined size of the absorbent product is placed in the side of the angular supporting cylinder 19. Other arrangements of the measuring device are the same as the aforementioned measuring device for use in measuring the diffusing absorbency under pressure.

The diffusing absorbency under pressure of the absorbent product was measured using the measuring device having the described arrangement in the following manner.

First, the absorbent product is formed with a size of 100 mm×100 mm. Then, predetermined preparatory operations were performed. Then, the filter paper 7 was placed on the glass filter 6, and the sheet 8 was placed on the filter sheet 7 in such a manner that its opening coincided with the center of the glass filter 6. Then, the angular supporting cylinder 19 was placed on the sheet 8 such that the central portion thereof coincided with the central portion of the glass filter 6.

Thereafter, the absorbent product was placed in the inside of the angular supporting cylinder 19, i.e., on the sheet 8, and the weight 11 was placed on the absorbent product. The placement operations of the absorbent product and the weight 11 were quickly performed.

Figure 7:
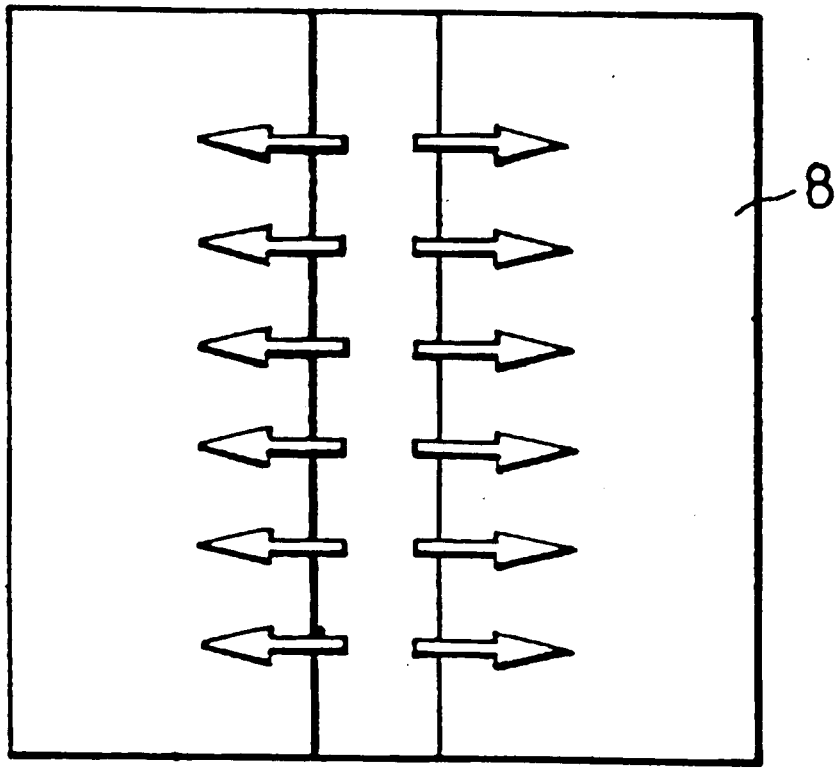
FIG. 7 is an explanatory view showing the diffusing direction of physiological saline solution in the measuring device of FIG. 5.

From the time at which the absorbent product was placed on the sheet 8, a weight $W_3$(g) of physiological saline solution 12 absorbed by the absorbent product was measured over 30 minutes or 60 minutes. In addition, as shown in FIG. 7, after passing through the opening of the sheet 8, the physiological saline solution 12 was absorbed by the absorbent product while the physiological saline solution 12 was being uniformly dispersed in the absorbent product in a lateral direction.

Then, based on the weight $W_3$, the diffusing absorbency under pressure (g/g) of the absorbent product was measured when 30 minutes or 60 minutes has elapsed after the absorption was started from the following formula:

Diffusing absorbency under pressure (g/g) of the Absorbent Product=Weight $W_3$ (g)/Weight (g) of the Absorbent Product.

The crosslinking agents used in Examples 1–6 and comparative examples 1–3 were prepared in the following manner.

Preparation 1

In an one-liter flask with four openings provided with an agitator, a water-separator with a cooling tube, a thermometer and an air-introducing tube, 134 g of trimethylolpropane, 238 g of acrylic acid, 170 g of toluene, 24 g of p-toluenesulfonic acid and 0.6 g of hydroquinone were fed, and the flask was heated to 130° C. while introducing air thereinto.

Produced water was distilled off from a reaction system by an azeotropic dehydration with toluene, while a reaction was performed for a predetermined time.

Then, the reaction solution was transferred to a separating funnel, and after neutralizing the unreacted acrylic acid with 500 g of 10 percent by weight of NaOH aqueous solution and 300 g of 5 percent by weight of NaOH aqueous solution, the reaction solution was layered and washed with water (500 g each) several times until the washed liquid was neutralized. Then, to an organic layer, 0.06 g of hydroquinone monomethyl ether was added, and the toluene was distilled under reduced pressure, thereby obtaining a reaction product.

The reaction product was analyzed using gas chromatography (GC), and gel permeation chromatography (GPC). As a result, the ratio of essential components of the cross-linking agent including trimethylolpropane triacrylate, trimethylolpropane diacrylate and trimethylolpropane diacrylatemono(β-acryloyloxypropionate) to a high boiling-point compound including a compound having at least two trimethylolpropane structures was 84/16. By the described reaction and operation, a cross-linking agent A having a ratio in weight of the essential component to the high boiling-point compound of 84/16 was obtained.

Preparation 2

The same reaction as preparation 1 was performed in the same manner except that the reaction time was set longer than preparation 1, and a cross-linking agent B having a ratio by weight of a cross-linking main component to a high-boiling point component of 78/22 was obtained.

Preparation 3

The same reaction as preparation 1 was performed in the same manner except that the reaction time was set shorter than preparation 1, and a cross-linking agent C having a ratio by weight of a cross-linking main component to a high-boiling point component of 89/11 was obtained.

Preparation 4

The same reaction as preparation 2 was performed in the same manner except that the reaction time was set still longer than preparation 2, and a comparative cross-linking agent having a ratio by weight of a comparative cross-linking main component to a high-boiling point component of 72/28 was obtained.

Next, using crosslinking agents obtained from Preparation 1–Preparation 4, a polymerization of a hydrophilic unsaturated monomer was performed in a solvent.

EXAMPLE 1

In 414 g of acrylic acid (hydrophilic unsaturated monomer), 4.8 g of the crosslinking agent A and 1.0 g of polyoxyethylenesorbitan monostearate (dispersant) were dissolved. To the mixture, 4382 g of 37 percent by weight of sodium acrylate (hydrophilic unsaturated monomer) and 551 g of ion exchanged water were added to give a reaction solution. In a stainless steel reactor of two-arms type kneader with a cover equipped with a jacket (volume content: 10 L) with two sigma blades, the reaction solution was poured, and the reaction system was displaced by introducing nitrogen gas while maintaining the reaction solution at 30° C. Then, while agitating the reaction solution maintained at 30° C., 2.40 g of sodium persulfate and 0.12 g of L-ascorbic acid were added to the reaction solution so as to start the polymerization. After leaving it for 40 minutes, a resulting finely divided water-containing gel-like polymer was taken out.

The resulting finely divided water-containing gel-like polymer was placed on a wire netting of 50 mesh and dried under hot air at 150° C. for 90 minutes. Then, the resulting dried polymer was pulverized by a vibrating mill and further classified by a wire netting of 20 mesh. As a result, an absorbent resin of undefined shape with a water content of 4 percent, an average particle diameter of 350 μm and ratio of particles having a diameter of 106 μm or below of 3 percent by weight was obtained. Namely, a precursor of the absorbing agent was obtained. The absorbency under pressure by tea bag method and the water soluble content of the resulting precursor of the absorbing agent (hereinafter simply referred to as results) are shown in Table 1.

EXAMPLE 2

The same reaction as Example 1 was performed in the same manner except that 4.8 g of the crosslinking agent B was used in place of the crosslinking agent A used in Example 1. As a result, an absorbent resin of undefined shape with a water content of 5 percent, an average particle diameter of 300 μm and ratio of particles having a diameter of 106 μm or below of 6 percent by weight was obtained. Namely, a precursor of the absorbing agent was obtained. The results of this example are shown in Table 1.

EXAMPLE 3

The same reaction as Example 1 was performed in the same manner except that 4.8 g of the crosslinking agent C was used in place of the crosslinking agent A used in Example 1. As a result, an absorbent resin of undefined shape with a water content of 8 percent, an average particle diameter of 480 μm and ratio of particles having a diameter of 106 μm or below of 0.5 percent by weight was obtained. Namely, a precursor of the absorbing agent was obtained. The results of this example are shown in Table 1.

EXAMPLE 4

The same reaction as Example 1 was performed in the same manner except that the amount of use of the crosslinking agent A was changed from 4.8 g to 6.8 g. As a result, an absorbent resin of undefined shape with a water content of 5 percent, an average particle diameter of 380 μm and ratio of particles having a diameter of 106 μm or below of 2 percent by weight was obtained. Namely, a precursor of the absorbing agent was obtained. The results of this example are shown in Table 1.

EXAMPLE 5

The same reaction as Example 1 was performed in the same manner except that the amount of use of the crosslinking agent A was changed from 4.8 g to 13.6 g. As a result, an absorbent resin of undefined shape with a water content of 4 percent, an average particle diameter of 400 μm and ratio of particles having a diameter of 106 μm or below of 1 percent by weight was obtained. Namely, a precursor of the absorbing agent was obtained. The results of this example are shown in Table 1.

EXAMPLE 6

In 29 g of acrylic acid (hydrophilic unsaturated monomer), 6.8 g of the crosslinking agent A and 2.3 g of partially saponified polyvinyl alcohol (dispersant) were dissolved. To the mixture, 4382 g of 37 percent by weight of sodium acrylate (hydrophilic unsaturated monomer), 385 g of acrylic acid (hydrophilic unsaturated monomer) and 283 g of ion exchanged water were added to give a reaction solution. Thereafter, the same reaction as Example 1 was performed. As a result, an absorbent resin of undefined shape with a water content of 8 percent, an average particle diameter of 520 μm and ratio of particles having a diameter of 106 μm or below of 0 percent by weight was obtained. Namely, a precursor of the comparative absorbing agent was obtained. The results of this example are shown in Table 1.

Comparative Example 1

The same reaction as Example 1 was performed in the same manner except that 4.8 g of comparative crosslinking agent was used in place of the crosslinking agent A used in Example 1. As a result, a comparative absorbent resin of undefined shape with a water content of 5 percent, an average particle diameter of 340 μm and ratio of particles having a diameter of 106 μm or below of 5 percent by weight was obtained. Namely, a precursor of the comparative absorbing agent was obtained. The results of this example are shown in Table 1.

Comparative Example 2

The same reaction as Example 1 was performed in the same manner except that polyoxyethylenesorbitan monostearate used in Example 1 was not used. As a result, a comparative absorbent resin of undefined shape with a water content of 4 percent, an average particle diameter of 370 μm and ratio of particles having a diameter of 106 μm or below of 3 percent by weight was obtained. Namely, a precursor of the comparative absorbing agent was obtained. The results of this example are shown in Table 1.

Comparative Example 3

The same reaction as Example 1 was performed in the same manner except that the amount of use of the crosslinking agent A was changed from 4.8 g to 2.0 g. As a result, an absorbent resin of undefined shape with a water content of 5 percent, an average particle diameter of 390 μm and ratio of particles having a diameter of 106 μm or below of 2 percent by weight was obtained. The results of this example are shown in Table 1.

TABLE 1

| | Absorbency by tea bag method (g/g) | Water soluble Content (% by weight) |
|---|---|---|
| Example 1 | 43 | 6 |
| Example 2 | 44 | 7 |
| Example 3 | 43 | 6 |
| Example 4 | 40 | 4 |
| Example 5 | 38 | 3 |
| Example 6 | 40 | 5 |
| Comparative Example 1 | 44 | 8 |
| Comparative Example 2 | 44 | 8 |
| Comparative Example 3 | 52 | 14 |

EXAMPLE 7

To 100 parts by weight of the precursor of the absorbing agent resulting from Example 1, a surface crosslinking agent composed of 0.5 parts by weight of glycerol (SP value: $\delta=16.5\ (cal/cm^3)^{1/2}$) as the first surface crosslinking agent, 0.1 parts by weight of ethylene glycol diglycidyl ether (SP value:$\delta=10.2\ (cal/cm^3)^{1/2}$) as the second crosslinking agent, 3 parts by weight of water and 1 part by weight of isopropyl alcohol was mixed. By applying a heat treatment to the resulting mixture for 40 minutes at 200° C., and absorbing agent was obtained. The absorbency by the tea bag method, the water soluble content, the diffusing absorbency under pressure and the absorbency under pressure of the absorbing agent (hereinafter simply referred to as results) are shown in Table 2.

EXAMPLES 8 AND 9

The same heat treatment as Example 7 was performed in the same manner except that 100 parts by weight of the precursor of the absorbing agents resulting from Examples 4 and 5 were used, and respective absorbing agents were obtained. The results of these examples are shown in Table 2.

Comparative Examples 4 and 5

The same heating process as Example 7 was performed in the same manner except that 100 parts by weight of the precursor of the comparative absorbing agents resulting from Comparative Examples 1 and 3 were used, and respective comparative absorbing agents were obtained. The results of these examples are shown in Table 2.

Comparative Example 6

A graft polymer of partially neutralized and crosslinked starch-acrylate (Sunwet IM3900P available from Hoechst Celanese Co., Ltd.) was used as a comparative absorbing agent. The results of this comparative example are shown in Table 2.

Comparative Example 7

A polymer of partially neutralized and crosslinked acrylate (Daiyawet US2-45Z; available from Mitsubishi Petrochemical Co., Ltd.) was used as a comparative absorbing agent. The results of this comparative example are shown in Table 2.

Comparative Example 8

A polymer of partially neutralized and crosslinked acrylate (Aquakeep SA-60; available from Sumitomo Seika Co., Ltd.) was used as a comparative absorbing agent. The results of this comparative example are shown in Table 2.

Comparative Example 9

A high-molecular absorbing agent was taken out from a paper diaper (Mammy poco available from Unicharm Co., Ltd.) as a comparative absorbing agent. The results of this comparative example are shown in Table 2.

TABLE 2

| | Absorbency (g/g) | Water Soluble Content (weight %) | Diffusing absorbency under pressure (g/g) After 20 min. | Diffusing absorbency under pressure (g/g) After 60 min. | Absorbency under pressure (ml/g) |
|---|---|---|---|---|---|
| Example 7 | 42 | 6 | 17 | 31 | 29 |
| Example 8 | 40 | 4 | 20 | 34 | 30 |
| Example 9 | 39 | 3 | 23 | 32 | 29 |
| Comp. Example 4 | 42 | 8 | 16 | 29 | 28 |
| Comp. Example 5 | 47 | 14 | 12 | 27 | 31 |
| Comp. Example 6 | 44 | 3 | 4 | 12 | 28 |
| Comp. Example 7 | 54 | 68 | 7 | 12 | 26 |
| Comp. Example 8 | 58 | 25 | 10 | 21 | 30 |
| Comp. Example 9 | 51 | 4 | 4 | 9 | 27 |

EXAMPLE 10

75 parts by weight of the absorbing agent obtained from Example 7 and 25 parts by weight of ground wood pulp (hydrophilic fiber) were mixed by a mixer using a dry method. The resulting mixture was formed into a web with a size of 100 mm×100 mm. Thereafter, by pressing the web for 1 minute with a pressure of 2 kg/cm$^2$, an absorbent product composed of an absorbent material with a basis weight of around 0.035 g/cm$^2$ was obtained. The diffusing absorbency under pressure of the resulting absorbent product when 60 minutes elapsed (hereinafter simply referred to as results) are shown in Table 3.

EXAMPLES 11 AND 12

An absorbent material was prepared in the same manner as Example 10 except that absorbing agents obtained from Examples 8 and 9 were used in place of the absorbing agent used in Example 10, and respective absorbent products were obtained. The results are shown in Table 3.

Comparative Examples 10–15

An absorbent material was prepared in the same manner as Example 10 except that absorbing agents obtained from Comparative Examples 4–9 were used in place of the absorbing agent used in Example 10, and respective absorbent products were obtained. The results are shown in Table 3.

TABLE 3

| | Diffusing absorbency under pressure of absorbent product when 60 min. elapsed (g/g) |
|---|---|
| Example 10 | 24.7 |
| Example 11 | 25.5 |
| Example 12 | 25.2 |
| Comparative Example 10 | 23.4 |
| Comparative Example 11 | 24.1 |
| Comparative Example 12 | 10.7 |
| Comparative Example 13 | 10.8 |
| Comparative Example 14 | 15.8 |
| Comparative Example 15 | 8.6 |

EXAMPLE 13

75 parts by weight of absorbing agent obtained from Example 7 and 75 parts by weight of groundwood pulp (hydrophilic fiber) were mixed by a mixer using a dry method. The resulting mixture was formed into a web using a batch-type pneumatic molding device which had a wire screen of 400 mesh, a web with a size of 120 mm×400 mm was formed. Further, by pressing the web for 5 seconds with a pressure of 2 kg/cm$^2$, an absorbent material with a basis weight of around 0.047 g/cm$^2$ was obtained.

Thereafter, by laminating a back sheet composed of polypropylene impermeable to liquid with a leg gather, the absorbent material and a top sheet made of polypropylene permeable to liquid in order using a both sided tape, and by putting two tape jippers to the adhesive material, an absorbent product (i.e., paper diaper) was obtained. The weight of the absorbent product was 46 g.

The absorbent product was put on a so-called Kewpie doll (height: 55 cm; and weight: 5 kg), and the doll was placed facing down. Thereafter, a tube was inserted between the absorbent product and the doll, and onto the position corresponding to the portion from which urine was to be discharged, 50 ml of physiological saline solution was poured each time, and a total amount of 250 ml of physiological saline solution was poured with an interval of 20 minutes. Then, after leaving the doll for 16 hours at 37° C., the absorbent product was taken out.

At the center of the absorbing portion of the absorbent product thus taken out, 10 pieces of so-called kitchen towels are laminated. Then, 10 kg was loaded on these kitchen towels for 1 minute, and the the amount of wet back of the kitchen towel, i.e., the obtained amount (g) of the physiological saline solution from the absorbent product was measured. The obtained result of this example is shown in Table 4.

EXAMPLES 14 AND 15

An absorbent product was prepared in the same manner as Example 13 except that absorbent agents obtained from Examples 8 and 9 were used in place of the absorbing agent used in Example 13. The obtained amount (g) of the physiological saline solution from the absorbent product was measured. The results of these examples are shown in Table 4.

Comparative Examples 16 and 17

An absorbent product was prepared in the same manner as Example 13 except that absorbent agents obtained from Comparative Examples 4 and 5 were used in place of the absorbing agent used in Example 13. The obtained amount (g) of the physiological saline solution from the absorbent material was measured. The results of these examples are shown in Table 4.

TABLE 4

| | Amount of Wet Back (g) |
|---|---|
| Example 13 | 3.1 |
| Example 14 | 2.3 |
| Example 15 | 0.7 |
| Comparative Example 15 | 6.6 |
| Comparative Example 17 | 9.2 |

As is clear from Tables 1–4, the absorbing agent of the present invention has high diffusing absorbency under pressure and low water soluble content. The absorbent product prepared using an absorbent material having high resin concentration has excellent properties (absorbent properties) also in that the amount of wet back of the aqueous liquid after a long time elapsed is small, and liquid diffusivity and stability with time of holding a constant amount of water (absorbing properties) are high.

EXAMPLE 16

To 5500 g of aqueous solution of 30 percent by weight of sodium acrylate (neutralization rate of 65 mole percent) as a monomer, was dissolved 18.49 g of polyethylene glycol diacrylate (average additional mole number of ethylene oxide=8) to prepare a reaction solution. Next, a deairing operation of the reaction solution was performed for 30 minutes under an atmosphere of nitrogen. In a stainless steel reactor of two-arms type kneader with a cover equipped with a jacket (volume content: 10 L) with two sigma blades, the reaction solution was poured, and the reaction system was displaced by introducing nitrogen gas while maintaining the reaction solution at 30° C. Then, while agitating the reaction solution, 2.30 g of ammonium sodium persulfate and 0.12 g of L-ascorbic acid were added to the reaction solution. As a result, the polymerization was started in one minute. Then, the polymerization was performed in one minute, and the polymerization reaction were performed at 30° C.–50° C., and the resulting water-containing gel-like polymer was taken out when 60 minutes elapsed after the polymerization started.

The resulting water-containing gel like polymer was finely divided into around 5 mm. The resulting finely divided water-containing gel-like polymer was placed on a wire netting of 50 mesh and dried under hot air at 150° C. for 90 minutes. Then, the resulting dried polymer was pulverized by a vibrating mill and further classified by a wire netting of 20 mesh. As a result, a precursor of the absorbing agent of undefined shape, an average particle diameter of 360 $\mu$m and ratio of particles having a diameter of 106 $\mu$m or below of 5 percent by weight was obtained.

To 100 parts by weight of precursor of the absorbing agent, a surface crosslinking agent composed of 1 part by weight of glycerol (SP value: $\delta$=16.5 $(cal/cm^3)^{1/2}$) as the first surface crosslinking agent and 0.05 parts by weight of ethylene glycol diglycidyl ether (SP value:$\delta$=10.2 $(cal/cm^3)^{1/2}$) as the second surface crosslinking agent, 3 parts by weight of water and 1 part by weight of ethyl alcohol were mixed. By applying a heat treatment to the resulting mixture for 40 minutes at 195° C., an absorbing agent was obtained. The resulting absorbing agent has an average particle diameter of 360 $\mu$m, and the ratio of the particles with a particle diameter of less than 106 $\mu$m was 5 percent by weight. The results of the water absorbing agent by the centrifugal separation method and the diffusing absorbency under pressure (hereinafter simply referred to as results) of the water absorbing agent are shown in Table 5.

EXAMPLE 17

To 5500 g per weight of 39 percent by weight of sodium acrylate (neutralization rate 75 percent), was dissolved 3.59 g of trimethylolpropane triacrylate as a crosslinking agent to prepare a reaction solution. Next, a deairing operation of the reaction solution was performed for 30 minutes under an atmosphere of nitrogen. Next, to the same reaction vessel as the reaction vessel of the Example 16, the reaction solution was supplied, and the reaction system was displaced by introducing nitrogen gas while maintaining the reaction solution at 30° C. Then, while agitating the reaction solution, 2.40 g of ammonium persulfate and 0.12 g of L-ascorbic acid were added to the reaction solution so as to start the polymerization, and a polymerization started after about 1 minute. The polymerization reaction was performed at 30° C.–80° C., and after leaving it for 60 minutes, a resulting finely divided water-containing gel-like polymer with a diameter of 5 mm was taken out.

The resulting finely divided water-containing gel-like polymer was placed on a wire netting of 50 mesh and dried under hot air at 150° C. for 90 minutes. Then, the resulting dried polymer was pulverized by a vibrating mill and further classified by a wire netting of 20 mesh. As a result, a precursor of the absorbing agent of undefined shape, an average particle diameter of 400 $\mu$m and ratio of particles having a diameter of 106 $\mu$m or below of 3 percent by weight was obtained.

To 100 parts by weight of the precursor of the absorbing agent, a surface crosslinking agent composed of 0.5 parts by weight of ethylene glycol (SP value: $\delta$=14.6 $(cal/cm^3)^{1/2}$) as the first surface crosslinking agent and 0.1 parts by weight of glycerol polyglycidyl ether (SP value: $\delta$=10.8 $(cal/cm^3)^{1/2}$), 3 parts by weight of water and 1 part by weight of ethyl alcohol were mixed. By applying a heat treatment to the resulting mixture for 40 minutes at 195° C., an absorbing agent was obtained. The resulting absorbing agent has an average particle diameter of 400 $\mu$m, and the ratio of the particles with a particle diameter of less than 106 $\mu$m was 3 percent by weight. The results of the water absorbing agent are shown in Table 5.

EXAMPLE 18

To 5500 g of 20 percent by weight of sodium acrylate, 2.35 g of N,N'-methylenebisacrylamide as a crosslinking agent was dissolved to prepare a reaction solution, Next, a deairing operation of the reaction solution was performed for 30 minutes under an atmosphere of nitrogen. Next, to the same reaction vessel as the reaction vessel of Example 16, the reaction solution was supplied, and the reaction system was displaced by introducing nitrogen gas while maintaining the reaction solution at 30° C. Then, while agitating the reaction solution maintained at 30° C., 1.5 g of ammonium persulfate and 0.07 g of L-ascorbic acid were added to the reaction solution. As a result, a polymerization started in about one minute. During the polymerization process, temperature was maintained in a range of 30° C.–80° C. After leaving it for 60 minutes, 606.7 of sodium carbonate (neutralizing agent) was further added, and the mixture was stirred. Then, a resulting water-containing gel-like polymer with a neutralization ratio of 75 mole percent was taken out.

The resulting water-containing gel-like polymer was finely divided into around 5 mm. The resulting finely divided water-containing gel-like polymer was placed on a wire netting of 50 mesh and dried under hot air at 150° C. for 90 minutes. Then, the resulting dried polymer was pulverized by a vibrating mill and further classified by a wire netting of 20 mesh. As a result, a precursor of the absorbing agent of undefined shape, an average particle diameter of 390 μm and ratio of particles having a diameter of 106 μm or below of 4 percent by weight was obtained.

To 100 parts by weight of the precursor of the absorbing agent, a surface crosslinking agent composed of 0.75 parts by weight of propylene glycol (SP value: $\delta=12.6$ $(cal/cm^3)^{1/2}$) as the first surface crosslinking agent and 0.05 parts by weight of propylene glycol diglycidyl ether (SP value: 67 =10.1 $(cal/cm^3)^{1/2}$) as the second surface crosslinking agent, 3 parts by weight of water and 0.75 part by weight of ethyl alcohol was mixed. By applying a heat treatment to the resulting mixture for 40 minutes at 195° C., an absorbing agent was obtained. The resulting absorbing agent has an average particle diameter of 390 μm, and the ratio of the particles with a particle diameter of less than 106 μm was 3 percent by weight. The results of the water absorbing agent are shown in Table 5.

Comparative Example 18

To 5500 g of 39 percent by weight of sodium acrylate (neutralization rate 75 percent), was dissolved 7.18 g of trimethylolpropane triacrylate as a crosslinking agent to prepare a reaction solution. Next, a deairing operation of the reaction solution was performed for 30 minutes under an atmosphere of nitrogen. Next, to the same reaction vessel as the reaction vessel of Example 16, the reaction solution was supplied, and the reaction system was displaced by introducing nitrogen gas while maintaining the reaction solution at 30° C. Then, while agitating the reaction solution maintained at 30° C., 5.0 g of sodium persulfate and 0.25 g of L-ascorbic acid were added to the reaction solution. As a result, a polymerization is started in about one minute. During the polymerization process, temperature is maintained in a range of 30° C.–80° C. After leaving it for 60 minutes, the resulting water-containing gel-like polymer was taken out.

The resulting water-containing gel-like polymer was finely divided into around 5 mm. The resulting finely divided water-containing gel-like polymer was placed on a wire netting of 50 mesh and dried under hot air at 150° C. for 90 minutes. Then, the resulting dried polymer was pulverized by a vibrating mill and further classified by a wire netting of 20 mesh. As a result, a comparative absorbing agent of undefined shape, an average particle diameter of 360 μm and ratio of particles having a diameter of 106 μm or below of 5 percent by weight was obtained. The results of the resulting comparative absorbing agent are shown in Table 5.

Comparative Example 19

The same reaction as comparative example 18 was performed in the same manner except that 18.67 g of N,N'-methylene bisacrylamide was used as a crosslinking agent in place of trimethylolpropane triacrylate used in Example 18. As a result, a comparative absorbing agent of undefined shape with an average particle diameter of 400 μm and a ratio of particles having a particle diameter of less than 106 μm of 3 percent by weight was obtained. The results of the resulting comparative absorbing agent are shown in Table 5.

Comparative Example 20

A partially neutralized and crosslinked acrylate polymer (aquaric CA. W4; Nippon Shokubai Co., Ltd.) was used as a comparative absorbing agent. The results of this comparative example are shown in Table 5.

Comparative Example 21

A partially neutralized and crosslinked starch-acrylate graft polymer (Sunwet IM3900P; Hoechst Celanese Co., Ltd.) was used as a comparative absorbing agent. The results of this comparative example are shown in Table 5.

Comparative Example 22

A partially neutralized and crosslinked acrylate polymer (Daiyawet US2-45Z; available from Mitsubishi Petrochemical Co., Ltd.) was used as a comparative absorbing agent. The results are shown in Table 5.

Comparative Example 23

A partially neutralized and crosslinked acrylate polymer (Aquakeep SA-60; available from Sumitomo Seika Co., Ltd.) was used as a comparative absorbing agent. The results are shown in Table 5.

Comparative Example 24

An absorbent resin was taken out from a paper diaper (Mammy poco available from Unicharm Co., Ltd.) and used as a comparative absorbing agent. The results of this comparative example are shown in Table 5.

TABLE 5

| | Absorbency by centrifuge | Diffusing absorbency under pressure (g/g) | | |
|---|---|---|---|---|
| | separation method | after 20 minutes | after 30 minutes | after 60 minutes |
| Example 16 | 31 | 20.8 | 28.6 | 31.3 |
| Example 17 | 30 | 22.5 | 27.9 | 30.1 |
| Example 18 | 38 | 16.0 | 24.0 | 33.9 |
| Comp. Example 18 | 31 | 3.6 | 5.9 | 11.7 |
| Comp. Example 19 | 18 | 10.1 | 16.7 | 21.1 |
| Comp. Example 20 | 40 | 20.3 | 22.1 | 23.1 |
| Comp. Example 21 | 33 | 4.2 | 6.5 | 11.7 |
| Comp. Example 22 | 37 | 6.9 | 9.7 | 12.2 |
| Comp. Example 23 | 39 | 9.6 | 13.9 | 21.1 |
| Comp. Example 24 | 32 | 3.7 | 5.7 | 9.1 |

EXAMPLE 19

45 parts by weight of the absorbing agent obtained from Example 16 and 55 parts by weight of groundwood pulp were mixed by a mixer using a dry method. The resulting mixture was formed into a web with a size of 100 mm×100 mm. Thereafter, by pressing the web for 1 minute with a pressure of 2 kg/cm$^2$, an absorbent product composed of an absorbent material with a basis weight of around 0.050 kg/cm$^2$ was obtained. The results of the diffusing absorbency under pressure of the absorbent material (hereinafter simply referred to as unit) are shown in Table 6.

EXAMPLE 20

50 parts by weight of absorbing agent obtained from Example 16 and 50 parts by weight of groundwood pulp were mixed by a mixer using a dry method. The resulting mixture was formed into a web with a size of 100 mm×100 mm. Thereafter, by pressing the web for one minute with a pressure of 2 kg/cm$^2$, an absorbent material with a basis weight of around 0.047 kg/cm$^2$ was obtained. The results of the absorbent material (hereinafter simply referred to as unit) are shown in Table 6.

EXAMPLE 21

60 parts by weight of the absorbing agent obtained from Example 16 and 40 parts by weight of groundwood pulp were mixed by a mixer using a dry method. The resulting mixture was formed into a web with a size of 100 mm×100 mm. Thereafter, by pressing the web for 1 minute under pressure of 2 kg/cm$^2$, an absorbent material with a basis weight of around 0.041 kg/cm$^2$ was obtained. The results of the absorbent material (hereinafter simply referred to as unit) are shown in Table 6.

EXAMPLE 22

75 parts by weight of the absorbing agent obtained from Example 16 and 25 parts by weight of groundwood pulp were mixed by a mixer using a dry method. The resulting mixture was formed into a web with a size of 100 mm×100 mm. Thereafter, by pressing the web for 1 minute with a pressure of 2 kg/cm$^2$, an absorbent material with a basis weight of around 0.035 kg/cm$^2$ was obtained. The results of the absorbent material are shown in Table 6.

EXAMPLES 23 AND 24

The same operation as Example 22 was performed in the same manner except that absorbing agents obtained from Examples 17 and 18 were used in place of the absorbing agent obtained from Example 16. The results of the absorbent material are shown in Table 6.

Comparative Example 25

The same operation as Example 19 was performed except that the comparative absorbing agent obtained from Comparative Example 18 was used in place of the absorbing agent obtained from Example 16. The results of the comparative absorbent material are shown in Table 6.

Comparative Example 26

The same operation as Example 20 was performed except that the comparative absorbing agent obtained from Comparative Example 18 was used in place of the absorbing agent obtained from Example 16. The results of the comparative absorbent material are shown in Table 6.

Comparative Example 27

The same operation as Example 21 was performed except that comparative absorbing agent obtained from Comparative Example 18 was used in place of the absorbing agent obtained from Example 16. The results of the comparative absorbent material are shown in Table 6.

Comparative Examples 28–34

The same operation as Example 22 was performed in the same manner except that comparative absorbing agents obtained from Comparative Examples 18–24 were used in place of the absorbing agent obtained from Example 16. The results of the comparative absorbent material are shown in Table 6.

TABLE 6

| | Diffusing absorbency under pressure of Absorbent material (g/g) | |
|---|---|---|
| | after 30 min. | after 60 min. |
| Example 19 | 19.4 | 19.7 |
| Example 20 | 19.5 | 20.1 |
| Example 21 | 19.3 | 22.2 |
| Example 22 | 19.1 | 24.3 |
| Example 23 | 19.4 | 23.1 |
| Example 24 | 17.9 | 25.6 |
| Comparative Example 25 | 17.6 | 18.5 |
| Comparative Example 26 | 10.1 | 15.1 |
| Comparative Example 27 | 9.6 | 14.2 |
| Comparative Example 28 | 7.3 | 10.4 |
| Comparative Example 29 | 13.0 | 16.9 |
| Comparative Example 30 | 16.0 | 18.3 |
| Comparative Example 31 | 7.4 | 10.7 |
| Comparative Example 32 | 9.1 | 10.7 |
| Comparative Example 33 | 11.5 | 15.8 |
| Comparative Example 34 | 6.8 | 8.6 |

EXAMPLE 25

50 parts by weight of absorbing agent obtained from Example 16 and 50 parts by weight of groundwood pulp were mixed with a mixer using a dry method. Next, to the resulting mixture, by performing a pneumatic molding using a batch-type pneumatic molding device on a wire screen formed with 400 mesh (38 $\mu$m), a web with 120 mm×400 mm size is formed. By pressing the web with a pressure of 2 kg/cm$^2$, for 5 seconds, an absorbent material with a weighting capacity of around 0.047 kg/cm$^2$ was obtained.

Thereafter, a so-called back sheet made of polypropylene which is impermeable to liquid, a back sheet having a leg gather (liquid impermeable sheet), the absorbent material, the top sheet made of polypropylene which is permeable to liquid (liquid permeable sheet) are formed by laminating them using a both-sided tape. By laminating these sheets using a both-sided tape, and mounting two tape fasteners on the adhering material, the absorbent product (a so-called paper diaper) was obtained. The weight of the absorbent product was 46 g.

The absorbent product was mounted on a so-called Cupy doll (height 55 cm and weight 5 kg), and the doll was placed facing down. Then, a tube was inserted between the absorbent product and the doll, and 50 ml of physiological saline solution was injected each time into the portion corresponding to the portion from which urea is to be discharged at an interval of 20 minutes. Then, when the physiological saline solution was not absorbed in the absorbent product and leaking, the described injecting operation was ended, and the amount of the absorbed physiological saline solution was measured.

After repeating the measurements four times, the average of the measurement was calculated, and the resulting value was determined as an absorbing amount. As a result, the absorbing amount of 250 g was obtained.

Comparative Example 35

The same reaction as Example 25 was performed in the same manner except that the comparative absorbing agent resulting from comparative example 18 was used in place of the absorbing agent from Example 16. The weight of the comparative absorbent product was 46 g.

Using the comparative absorbent product, the same operation as Example 25 was repeated four times, and thereafter, the average of the resulting measurement value was calculated, and the value was determined as an absorbing amount. As a result, the absorbing amount of 255 g was obtained.

As is clear from the results described in Table 5 and Table 6, the absorbing agent and the absorbent material of the present invention has high diffusing absorbency under pressure and very high diffusivity to liquid. The difference in absorbent properties of the absorbing agent and the absorbent material between the present invention and comparative examples becomes greater as the resin concentration of the absorbent material becomes greater. As is clear from the results described in Example 25 and comparative Example 35, the absorbent property of the absorbent product of the present invention shows excellent properties (absorbent properties) such as very high absorbing amount (absorbing capacity) as compared to the comparative absorbent product.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

[Possible Industrial Applications]

The absorbing agent and the absorbent material are suitably applied essentially to thinner absorbent products such as a paper diaper, a sanitary napkin of higher performances, etc. As a result, the present invention provides absorbent products having excellent performances.

What is claimed is:

1. An absorbing agent formed from a precursor prepared by [performing an aqueous solution] polymerization of a hydrophilic unsaturated monomer having [at least 50 mole percent neutralized] *an* acrylic acid *and/or an acrylic acid salt* as a main component, and having a crosslinked density in the vicinity of a surface of said agent higher than a crosslinked density at an inside portion thereof, said absorbing agent having a diffusing absorbency under pressure of not less than [25] *30* g/g when 60 minutes have elapsed after absorption has started.

2. [An] *The* absorbing agent [formed from a precursor prepared by performing an aqueous solution polymerization of a hydrophilic unsaturated monomer having at least 50 mole percent neutralized acrylic acid as a main component, and having a crosslinked density in the vicinity of a surface of said agent higher than a crosslinked density at an inside portion thereof, said absorbing agent having] *as set forth in claim 1, wherein* a diffusing absorbency under pressure [of] is not less than [15] *32* g/g when [30] *60* minutes have elapsed after absorption has started.

3. The absorbing agent as set forth in claim [2] *1*, wherein:

a diffusing absorbency under pressure is not less than [25] *34* g/g when 60 minutes *have* elapsed after absorption has started.

4. [An] *The* absorbing agent [formed from a precursor prepared by performing an aqueous solution polymerization of a hydrophilic unsaturated monomer having at least 50 mole percent neutralized acrylic acid as a main component, and having a crosslinked density in the vicinity of a surface of said agent higher than a crosslinked density at an inside portion thereof, said absorbing agent having] *as set forth in claim 1, wherein* a diffusing absorbency under pressure [of] *is* not less than 15 g/g when [20] *30* minutes have elapsed after absorption has started.

5. The absorbing agent as set forth in claim [4] *1*, wherein:

a diffusing absorbency under pressure is not less than [25] *15* g/g when [60] *20* minutes *have* elapsed after absorption has started.

[6. The absorbing agent as set forth in claim 4, wherein:

a diffusing absorbency under pressure is not less than 30 g/g when 60 minutes elapsed after absorption has started.]

7. The absorbing agent as set forth in claim 1, wherein:

a water soluble component amount is above 0 and not more than 7 percent by weight.

8. The absorbing agent as set forth in claim 1, containing a dispersant.

9. The absorbing agent as set forth in claim 8, wherein:

said dispersant is contained in an amount in a range of 0.005 parts by weight to 0.5 parts by weight with respect to 100 parts by weight of [a] *the* precursor of the absorbing agent, *composed of a monomer*.

10. An absorbent material, comprising:

*an absorbing agent in an amount of* not less than 40 percent by weight [of an absorbing agent formed from a precursor prepared by performing an aqueous solution polymerization of a hydrophilic unsaturated monomer having at least 50 mole percent neutralized acrylic acid as a main component, and having a cross-linked density in the vicinity of a surface of said agent higher than a crosslinked density at an inside portion thereof], said absorbing agent having a diffusing absorbency under pressure of [25] *not less than 30* g/g when 60 minutes have elapsed after absorption has started.

11. The absorbent material as set forth in claim 10, wherein:

*said absorbing agent has* a diffusing absorbency under pressure [is] *of* not less than [15] *32* g/g when [30] *60* minutes *have* elapsed after absorption has started.

12. The absorbent material as set forth in claim 10, further comprising:

a hydrophilic fiber.

13. The absorbent material as set forth in claim 12, wherein:

said hydrophilic fiber is contained in an amount in a range of above 0 percent by weight and not more than 60 percent by weight.

14. The absorbent material as set forth in claim 12, wherein:

said absorbing agent is contained in an amount of not less than 50 percent by weight with respect to a total amount of said absorbing agent and said hydrophilic fiber.

15. The absorbent material as set forth in claim 10, further comprising:

an adhesive binder.

16. An absorbent product, comprising:

an absorbent material including an absorbing agent [formed from a precursor prepared by performing an aqueous solution polymerization of a hydrophilic unsaturated monomer having at least 50 mole percent neutralized acrylic acid as a main component, and having a cross-linked density in the vicinity of a surface of said agent higher than a crosslinked density at an inside portion thereof, said absorbing agent] having a diffusing absorbency under pressure of not less than [25] *30* g/g when 60 minutes have elapsed after absorption has started, and a water soluble [content in a range of greater than] *component amount of above* 0 [percent by weight] and not more than 7 percent by weight.

17. The absorbent product as set forth in claim 16, wherein:

said [absorbent material] *absorbing agent further* contains a hydrophilic fiber in an amount in a range of above 0 percent by weight and not more than 60 percent by weight *with respect to said absorbing agent*.

18. The absorbent product as set forth in claim 17, wherein:

[said absorbent material includes] said hydrophilic fiber *is contained* in an amount in a range [between] 20 percent by weight [and] *to* 40 percent by weight *with respect to said absorbing agent*.

19. The absorbent product as set forth in claim 16, wherein:

said absorbent material further [includes] *contains* an adhesive binder.

20. An absorbent product comprising:

an absorbing layer [of claim 1 including an absorbent material being] sandwiched between a sheet which is permeable to liquid and a sheet which is impermeable to liquid*, said absorbing layer containing an absorbing agent having a diffusing absorbency under pressure of not less than 30 g/g when 60 minutes have elapsed after absorption has started*.

21. A process of manufacturing an absorbing agent, comprising the steps of:

performing an aqueous solution polymerization of a hydrophilic unsaturated monomer having at least 50 mole percent neutralized acrylic acid as a main component in a presence of a dispersant *to prepare a precursor of said absorbing agent*, using a crosslinking agent composed of a main component and a high-boiling point component in a range of not less than 0.05 mole percent and not more than 0.5 mole percent with respect to a total amount of said hydrophilic unsaturated monomer, wherein a ratio in weight of the main component of said crosslinking agent to said high-boiling point component is in a range of 75/25 to 99/1, said main component of said crosslinking agent is composed of an ester compound including a [polyhydroxy] *polyvalent* alcohol having not more than six carbon atoms and at least three hydroxy groups and an unsaturated carboxylic acid, a ratio in molecular weight of the main component of said crosslinking agent to [the] *a* standard compound is in a range of not less than 0.7 and less than 1.3 based on [a] *the* molecular weight of [a] *the* standard compound wherein all hydroxy group of the polyvalent alcohol are ester-linked to the unsaturated carboxylic acid, and said high-boiling point component includes at least two alcohol structures in a molecule;

adjusting said precursor of said absorbing agent so as to have a water content of not more than 10 percent, an average particle diameter in a range of 200 $\mu$m–600 $\mu$m, and a ratio of particles having a diameter of not more than 106 $\mu$m of not more than 10 percent by weight; and applying a heat treatment to said precursor of said absorbing agent in a presence of a surface crosslinking agent.

22. The process of manufacturing the absorbing agent as set forth in claim 21, wherein:

said surface crosslinking agent is composed of a first surface crosslinking agent reactive to a carboxyl group having a solubility parameter (SP value) of not less than 12.5 $(cal/cm^3)^{1/2}$ and a second surface crosslinking agent having a solubility parameter of less than 12.5 $(cal/cm^3)^{1/2}$; and the heat treatment is performed at *a* temperature of not less than 160° C.

*23. The absorbent material as set forth in claim 10, wherein:*

*said absorbing agent has a diffusing absorbency under pressure of not less than 34 g/g when 60 minutes have elapsed after absorption has started.*

*24. The absorbent material as set forth in claim 10, wherein:*

*said absorbing agent has a diffusing absorbency under pressure of not less than 15 g/g when 30 minutes have elapsed after absorption has started.*

*25. The absorbent material as set forth in claim 10, wherein:*

*said absorbing agent has a diffusing absorbency under pressure of not less than 15 g/g when 20 minutes have elapsed after absorption has started.*

*26. The absorbent material as set forth in claim 16, wherein:*

*said absorbing agent has a diffusing absorbency under pressure of not less than 32 g/g when 60 minutes have elapsed after absorption has started.*

*27. The absorbent material as set forth in claim 16, wherein:*

*said absorbing agent has a diffusing absorbency under pressure of not less than 34 g/g when 60 minutes have elapsed after absorption has started.*

*28. The absorbent material as set forth in claim 16, wherein:*

*said absorbing agent has a diffusing absorbency under pressure of not less than 15 g/g when 30 minutes have elapsed after absorption has started.*

*29. The absorbent material as set forth in claim 16, wherein:*

*said absorbing agent has a diffusing absorbency under pressure of not less than 15 g/g when 20 minutes have elapsed after absorption has started.*

*30. The absorbing agent as set forth in claim 1,*

*said agent is prepared by applying a heat treatment to a precursor having an internal crosslinking structure in the presence of a first surface crosslinking agent having a solubility parameter (SP value) of not less than 12.5 $(cal/cm^3)^{1/2}$ and a second surface crosslinking agent having a solubility parameter of less than 12.5 $(cal/cm^3)^{1/2}$.*

* * * * *

UNITED STATES PATENT AND TRADEMARK OFFICE

CERTIFICATE OF CORRECTION

PATENT NO. : RE 38,444 E
DATED : February 24, 2004
INVENTOR(S) : Katsuyuki Wada et al.

It is certified that error appears in the above-identified patent and that said Letters Patent is hereby corrected as shown below:

Title page,
Item [22], PCT Filed, "Dec. 28, 1995" should be -- Jun. 9, 1995 --.
Item [86], § 371 (c )(1), (2), (4) Date, "Jun. 9, 1995" should be -- Dec. 28, 1995 --.

Signed and Sealed this

Twenty-second Day of March, 2005

JON W. DUDAS
*Director of the United States Patent and Trademark Office*